(12) United States Patent
Yugawa

(10) Patent No.: US 11,615,893 B2
(45) Date of Patent: Mar. 28, 2023

(54) METHOD FOR EVALUATING INFECTION RISK, INFECTION RISK EVALUATION SYSTEM, AND MEDIUM

(71) Applicant: Panasonic Intellectual Property Management Co., Ltd., Osaka (JP)

(72) Inventor: Keiko Yugawa, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 279 days.

(21) Appl. No.: 17/033,681

(22) Filed: Sep. 26, 2020

(65) Prior Publication Data

US 2021/0012905 A1    Jan. 14, 2021

Related U.S. Application Data

(63) Continuation of application No. PCT/JP2019/024054, filed on Jun. 18, 2019.

(30) Foreign Application Priority Data

Jul. 13, 2018  (JP) .............................. JP2018-133390

(51) Int. Cl.
    *G16H 50/30*    (2018.01)
    *G16H 10/60*    (2018.01)

(52) U.S. Cl.
    CPC .............. *G16H 50/30* (2018.01); *G16H 10/60* (2018.01)

(58) Field of Classification Search
None
See application file for complete search history.

(56) References Cited

U.S. PATENT DOCUMENTS

| | | | |
|---|---|---|---|
| 11,342,051 B1 * | 5/2022 | Jain | ........................ G16H 10/60 |
| 2009/0265106 A1 * | 10/2009 | Bearman | .................. G06N 5/02 |
| | | | 701/300 |

(Continued)

FOREIGN PATENT DOCUMENTS

JP    2011-065540    3/2011

OTHER PUBLICATIONS

Extended European Search Report dated Aug. 10, 2021 in related European Patent Application No. 19833150.6.

(Continued)

*Primary Examiner* — Jonathan Ng
(74) *Attorney, Agent, or Firm* — Wenderoth, Lind & Ponack, L.L.P.

(57) ABSTRACT

A method for evaluating an infection risk includes calculating a first infection risk value, which indicates a degree of an infection risk that a child is infected with an infectious disease, on the basis of infection information regarding family members, prevalence information regarding the infectious disease in organizations to which the family members belong, and one or more first infection risk coefficients, calculating, on the basis of the first infection risk value, a second infection risk value, which indicates a degree of the child's infection risk of being infected in a group at a children's facility, and performing first evaluation, in which the infection risk that the child is infected is evaluated on the basis of the first infection risk value, and second evaluation, in which the child's infection risk of being infected in the group is evaluated on the basis of the second infection risk value.

12 Claims, 17 Drawing Sheets

(56) References Cited

U.S. PATENT DOCUMENTS

| | | | | |
|---|---|---|---|---|
| 2011/0184250 A1* | 7/2011 | Schmidt | ................ | G16Z 99/00 600/300 |
| 2013/0318027 A1* | 11/2013 | Almogy | ................ | G16H 50/20 706/52 |
| 2014/0167917 A2* | 6/2014 | Wallace | ................ | G16H 40/67 340/10.1 |
| 2015/0339585 A1* | 11/2015 | Ding | ................ | G16Z 99/00 706/12 |
| 2017/0209102 A1* | 7/2017 | Parthasarathy | ...... | A61B 5/0059 |
| 2021/0050116 A1* | 2/2021 | Sabeti | ................ | G16H 50/50 |

OTHER PUBLICATIONS

International Search Report of PCT application No. PCT/JP2019/024054 dated Aug. 20, 2019.

* cited by examiner

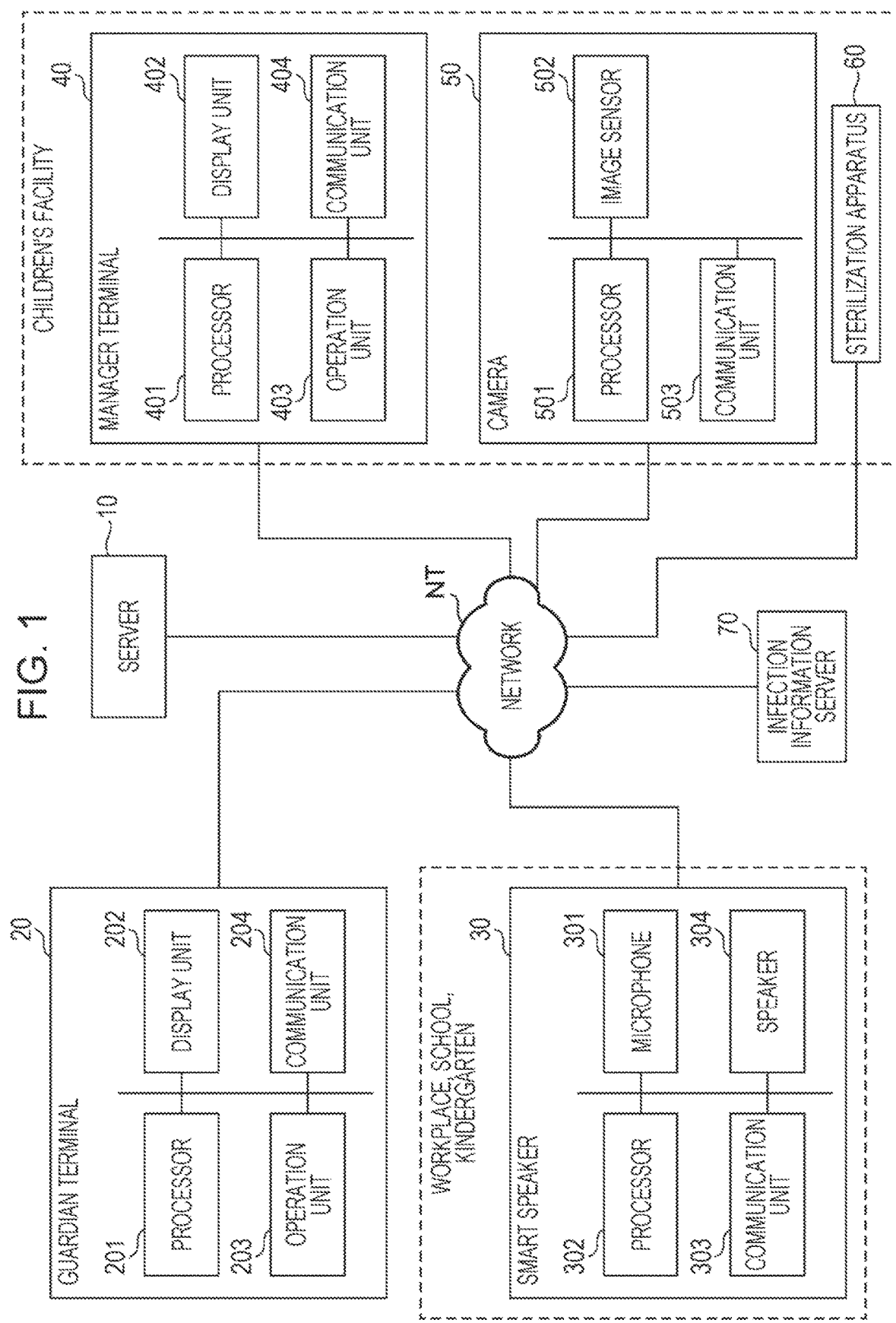

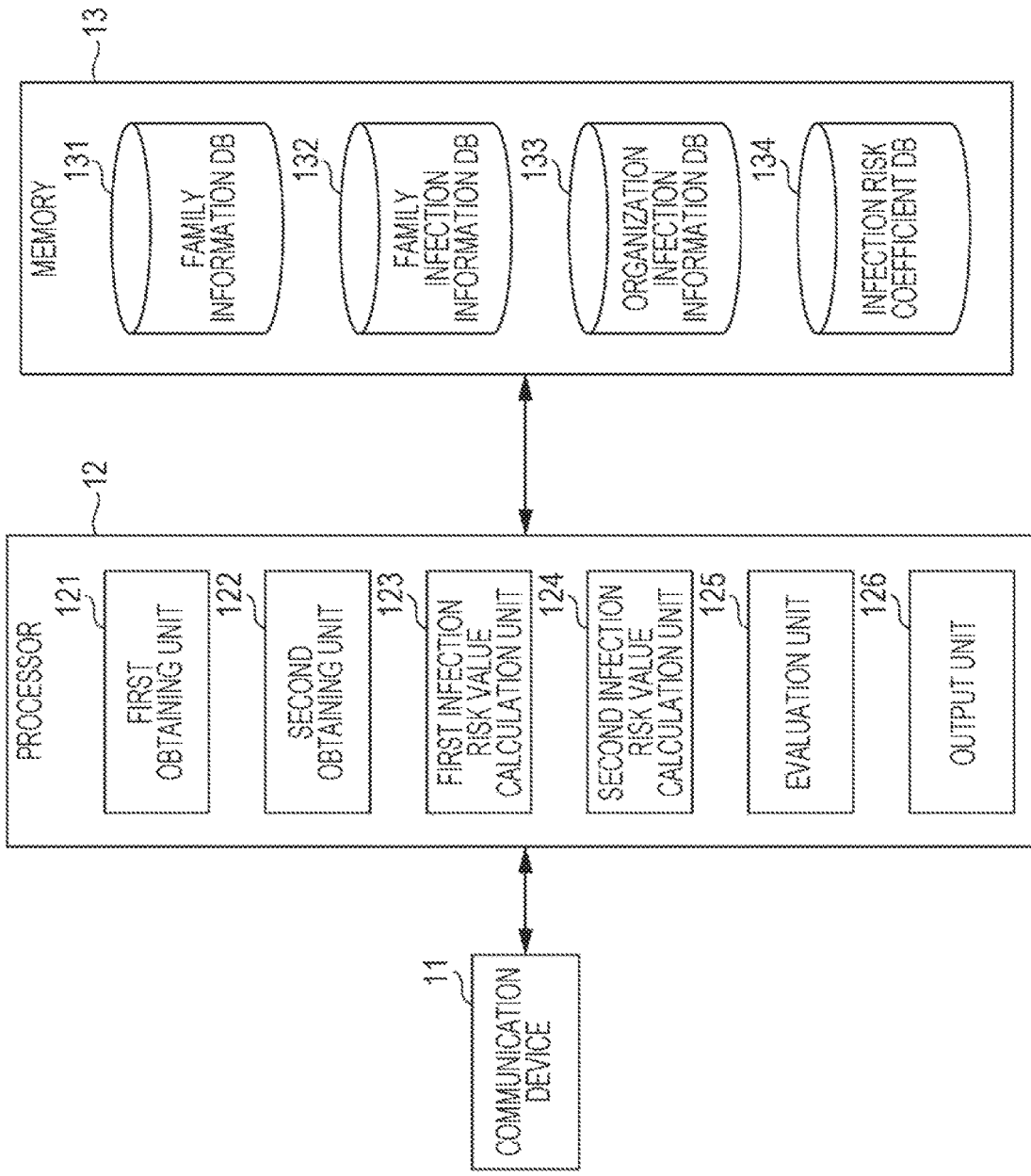

| FAMILY INFORMATION | | ~131A |
| --- | --- | --- |
| NAME | ABC | |
| NICKNAME | A | |
| AGE | 3 | |
| CLASS | DANDELION | |
| FACE | IMAGE | |
| LIVE WITH | FATHER | |
| | MOTHER | |
| | ELDER BROTHER | |
| | YOUNGER BROTHER | |

| FAMILY INFORMATION | | ~131B |
| --- | --- | --- |
| RELATIONSHIP | FATHER | |

| FAMILY INFORMATION | | ~131C |
| --- | --- | --- |
| RELATIONSHIP | MOTHER | |

| FAMILY INFORMATION | | ~131D |
| --- | --- | --- |
| RELATIONSHIP | ELDER BROTHER | |
| NAME | ABC | |
| NICKNAME | TARO | |
| AGE | 8 | |
| BELONGING | A ELE... | |

| FAMILY INFORMATION | | ~131E |
| --- | --- | --- |
| RELATIONSHIP | YOUNGER BROTHER | |
| NAME | ABC | |
| NICKNAME | JIRO | |
| AGE | 1 | |
| BELONGING | B NURSERY SCHOOL | |

| | FATHER | | MOTHER | | ELDER BROTHER | | YOUNGER BROTHER | |
|---|---|---|---|---|---|---|---|---|
| | INFECTION | BELONGING | INFECTION | BELONGING | INFECTION | BELONGING | INFECTION | BELONGING |
| 2018/1/9 | 1 | 0 | 0 | 0 | 0 | 1 | 1 | 1 |
| TODAY (2018/1/10) | 1 | 0 | 0 | 0 | 0 | 1 | 1 | 1 |
| 2018/1/11 | | | | | | | | |

|  |  | OVERALL | FATHER | MOTHER | ELDER BROTHER | YOUNGER BROTHER |
|---|---|---|---|---|---|---|
| FAMILY | RF | 1 | 0.3 | 0.8 | 0.5 | 1 |
| BELONGING | RM | 0.3 | 0.1 | 0.1 | 0.5 | 1 |

FIG. 7

|  |  | FATHER | MOTHER | ELDER BROTHER | YOUNGER BROTHER |
|---|---|---|---|---|---|
| FAMILY | DF | 1 | 0 | 0 | 1 |
| BELONGING | DM | 0 | 0 | 1 | 1 |

FIG. 10

| | PERIOD | P1 | P2 | P3 | P4 | P5 | EASTERN | TOTAL |
|---|---|---|---|---|---|---|---|---|
| 1 | (12/26 - 1/1) | 0 | 4 | 7 | 9 | 2 | 15 | 37 |
| 2 | (1/2 - 1/8) | 3 | 1 | 1 | 1 | 1 | 0 | 7 |
| 3 | (1/9 - 1/15) | 5 | 1 | 0 | 2 | 0 | 3 | 11 |
| 4 | (1/16 - 1/22) | 0 | 7 | 4 | 2 | 2 | 4 | 19 |
| 5 | (1/23 - 1/29) | 0 | 3 | 2 | 4 | 2 | 4 | 15 |
| 6 | (1/30 - 2/5) | 1 | 3 | 0 | 2 | 1 | 4 | 11 |
| 7 | (2/6 - 2/12) | 3 | 3 | 0 | 3 | 0 | 4 | 13 |
| 8 | (2/13 - 2/19) | 9 | 2 | 2 | 0 | 0 | 2 | 15 |
| 9 | (2/20 - 2/26) | 4 | 0 | 0 | 11 | 0 | 2 | 17 |
| 10 | (2/27 - 3/5) | 6 | 0 | 2 | 5 | 1 | 3 | 17 |
| 11 | (3/6 - 3/12) | 9 | 2 | 3 | 6 | 2 | 11 | 33 |
| 12 | (3/13 - 3/19) | 3 | 1 | 0 | 5 | 1 | 3 | 13 |
| 13 | (3/20 - 3/26) | 3 | 2 | 0 | 1 | 1 | 9 | 16 |
| 14 | (3/27 - 4/2) | 1 | 4 | 0 | 11 | 0 | 2 | 18 |
| 15 | (4/3 - 4/9) | 3 | 3 | 1 | 8 | 1 | 8 | 24 |

METHOD FOR EVALUATING INFECTION RISK, INFECTION RISK EVALUATION SYSTEM, AND MEDIUM

BACKGROUND

1. Technical Field

The present invention relates to a technique for evaluating an infection risk by an infectious disease in a children's facility.

2. Description of the Related Art

In Japanese Unexamined Patent Application Publication No. 2011-65540, a health management system that, when a pandemic occurs, automatically determines whether each of employees may go to work without requiring the employee to determine whether to go to work is disclosed.

More specifically, in this example of the related art, a management target is asked to input health state information such as a body temperature, a physical condition, and health states of family members, the input health state information is compared with work possibility determination reference information, whether the management target may go to work is determined in accordance with an applicable pattern of a work possibility determination, and the management target is notified of a result of the determination.

SUMMARY

Because an infection risk that a child is infected with an infectious disease and the child's infection risk of being infected with the infectious disease in a group at a children's facility to which the child belongs are not calculated in Japanese Unexamined Patent Application Publication No. 2011-65540, however, further improvements need to be made.

In one general aspect, the techniques disclosed here feature a method for evaluating an infection risk in an infection risk evaluation system that evaluates an infection risk by an infectious disease in a children's facility. A computer of the infection risk evaluation system performs a process including obtaining infection information, which is information regarding a condition of infection of each of one or more family members of a child with the infectious disease, obtaining prevalence information, which is information regarding a condition of prevalence of the infectious disease in one or more organizations to which the one or more family members belong, calculating a first infection risk value, which indicates a degree of an infection risk that the child is infected with the infectious disease, on a basis of the infection information, the prevalence information, and one or more first infection risk coefficients, which are obtained by expressing infection risks between the child and the one or more family members in numbers, calculating, on a basis of the first infection risk value, a second infection risk value, which indicates a degree of the child's infection risk of being infected with the infectious disease in a group at the children's facility to which the child belongs, performing at least either first evaluation, in which the first infection risk value is compared with a certain first reference value and the infection risk that the child is infected with the infectious disease is evaluated, and second evaluation, in which the second infection risk value is compared with a certain second reference value and the child's infection risk of being infected with the infectious disease in the group is evaluated; and outputting an evaluation result of at least either the first evaluation or the second evaluation.

According to the present disclosure, a child's infection risk of being infected with an infectious disease in a group and an infection risk that the child is infected with the infectious disease can be accurately estimated.

It should be noted that this general or specific aspect may be implemented as an apparatus, a system, an integrated circuit, a computer program, a computer-readable storage medium, or any selective combination thereof. The computer-readable storage medium may be a nonvolatile storage medium such as a compact disc read-only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 1 is a diagram illustrating an example of the overall configuration of an infection risk evaluation system according to an embodiment of the present disclosure;

FIG. 2 is a block diagram illustrating an example of the configuration of a server illustrated in FIG. 1;

FIG. 3 is a diagram illustrating an example of the data structure of a family information database (DB);

FIG. 4 is a diagram illustrating an example of the data structure of a family infection information DB;

FIG. 6 is a diagram illustrating an example of the data structure of an infection risk coefficient DB;

FIG. 7 is a table used to describe a specific example of first infection risk values;

FIG. 10 is a diagram illustrating an example of the data structure of area infection information;

DETAILED DESCRIPTION

Circumstances Behind Conception of Present Disclosure

Figure 5:
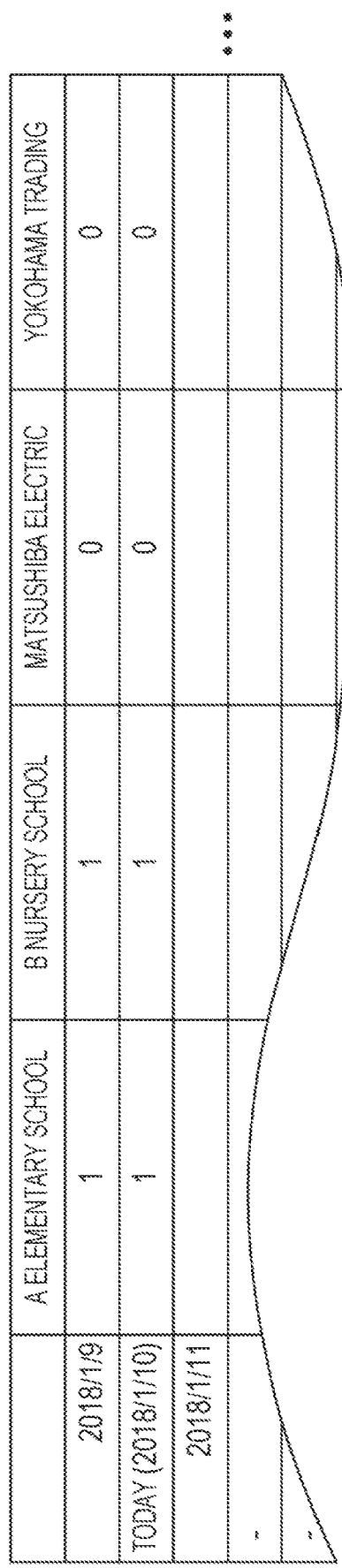
FIG. 5 is a diagram illustrating an example of the data structure of an organization infection information DB.

When an infectious disease such as norovirus or influenza becomes prevalent in a children's facility such as a kindergarten, a day nursery, a nursery school, or an elementary school, the infectious disease undesirably affects a lot of children. Prevalence of an infectious disease, therefore, needs to be prevented, or even after an infectious disease becomes prevalent, the prevalence needs to be minimized. For this purpose, a child's infection risk of being infected with an infectious disease in a group to which the child belongs, such as a class, needs to be accurately estimated and a guardian of the child needs to be notified of the infection risk, and an infection risk that the child is infected with the infectious disease needs to be accurately estimated and a manager of a children's facility needs to be notified of the infection risk.

Here, infection of a child with an infectious disease depends not only on a physical condition of the child and physical conditions of family members of the child but also presence or absence of prevalence of the infectious disease in organizations (e.g., a company, a school, a kindergarten, a nursery school, etc.) to which the family members belong. In addition, in order to accurately estimate an infection risk in a group to which a child belongs, not only an infection risk of each of children needs to be individually evaluated but also an infection risk of each of the children needs to be comprehensively evaluated.

In the above-described Japanese Unexamined Patent Application Publication No. 2011-65540, however, only health state information such as a body temperature, a physical condition, and health states of family members input by a management target and predetermined work possibility determination reference information are compared with each other, and presence or absence of prevalence of an infectious disease in organizations to which the family members of the management target belong is not taken into consideration at all, Even when the technique in this example of the related art is employed for a children's facility, therefore, it is difficult to accurately estimate an infection risk that a child is infected with an infectious disease and the child's infection risk of being infected in a group.

Furthermore, in this example of the related art, although health states of family members are taken into consideration, how easily an infectious disease can spread between a management target and the family members is not taken into consideration. In the case of a family including a housewife, for example, a mother and brothers of a target child are physically closer to the target child than a father is, and the target child's infection risk of catching an infectious disease from the mother and the brothers is higher than from the farther. Even when this example of the related art is employed for the target child, therefore, it is difficult to accurately estimate an infection risk of the target child.

The present disclosure provides a method for evaluating an infection risk and the like capable of accurately estimating a child's infection risk of being infected in a group and an infection risk that the child is infected with the infectious disease.

An aspect of the present disclosure is a method for evaluating an infection risk in an infection risk evaluation system that evaluates an infection risk by an infectious disease in a children's facility, a computer of the infection risk evaluation system performing a process including:

obtaining infection information, which is information regarding a condition of infection of each of one or more family members of a child with the infectious disease;

obtaining prevalence information, which is information regarding a condition of prevalence of the infectious disease in one or more organizations to which the one or more family members belong;

calculating a first infection risk value, which indicates a degree of an infection risk that the child is infected with the infectious disease, on a basis of the infection information, the prevalence information, and one or more first infection risk coefficients, which are obtained by expressing infection risks between the child and the one or more family members in numbers;

calculating, on a basis of the first infection risk value, a second infection risk value, which indicates a degree of the child's infection risk of being infected with the infectious disease in a group at the children's facility to which the child belongs;

performing at least either first evaluation, in which the first infection risk value is compared with a certain first reference value and the infection risk that the child is infected with the infectious disease is evaluated, and second evaluation, in which the second infection risk value is compared with a certain second reference value and the child's infection risk of being infected with the infectious disease in the group is evaluated; and outputting an evaluation result of at least either the first evaluation or the second evaluation.

With this configuration, a first infection risk value is calculated using not only infection information regarding family members of a child but also prevalence information regarding an infectious disease for the family members and first infection risk coefficients between the child and the family members. An infection risk that the child is infected with the infectious disease, therefore, can be accurately estimated.

In addition, a second infection risk value is calculated using the first infection risk value. The child's infection risk of being infected with the infectious disease in a group at a children's facility to which the child belongs can be accurately estimated.

In addition, at least either first evaluation in which the first infection risk value is compared with a first threshold, or second evaluation, in which the second infection risk value is compared with a second threshold, is performed, and a result of the evaluation is output. When a result of the first evaluation is output, a manager of the group who has seen the result of the first evaluation can suppress prevalence of the infectious disease in the group by, for example, preventing a child whose infection risk is high from becoming physically close to other children or asking a child whose infection risk is high not to attend the group.

When a result of the second evaluation is output, a guardian who has seen the result of the second evaluation can prevent the child from being infected with the infectious disease by, for example, making the child stay away from the group.

In the above aspect, with each of the one or more family members, a first value, which indicates that the family member is infected with the infectious disease, and a second value, which indicates that the infectious disease is prevalent in the corresponding organization, may be associated in the infection information at certain time intervals. The first infection risk value may be calculated by adding up, at the certain time intervals, a first sum of one or more first products of the one or more first values and the one or more first infection risk coefficients corresponding to the one or more first values of all of the one or more family members and a second sum of one or more second products of the one or more second values and the one or more second infection risk coefficients corresponding to the one or more second values of all of the one or more family members. The one or more second infection risk coefficients may be obtained by expressing, for the one or more family members, the infection risks in relation to the one or more organizations in numbers.

With this configuration, a first sum of first products=first values, each of which indicates that a family member is infected with an infectious disease, ×first infection risk coefficients of the family members calculated for all the family members is calculated at certain time intervals. In addition, a second sum of second products=second values, each of which indicates that the infectious disease is prevalent in an organization to which a family member belongs, ×second infection risk coefficients of the family members calculated for all the family members is calculated at the certain time intervals. A value obtained by adding up the first sum and the second sum at the certain time intervals is then calculated as a first infection risk value. The first infection risk value can therefore be accurately calculated at the certain time intervals.

In the above aspect, the second infection risk value may be obtained by calculating, at the certain time intervals, a sum of first infection risk values calculated for children belonging to the group or an average of the sum.

With this configuration, the second infection risk value can be accurately calculated at the certain time intervals.

In the above aspect, in a case where the first infection risk value tends to increase, the first infection risk value may be increased through correction, and in a case where the first infection risk value tends to decrease, the first infection risk value may be decreased through correction.

With this configuration, when the first infection risk value calculated at the certain time intervals tends to increase and the infectious disease is spreading, the first infection risk value is increased. When the first infection risk value calculated at the certain time intervals tends to decrease and the infectious disease is being eradicated, the first infection risk value is decreased. As a result, the first infection risk value can be calculated while taking into consideration whether the infectious disease is spreading or being eradicated.

The above aspect may further include obtaining a result of recognition of a sound performed by a sound recognition apparatus installed in each of the one or more organizations. The prevalence information may include, for each of the one or more organizations, a third value, which indicates prevalence of the infectious disease; determined at the certain time intervals using the result of the recognition of a sound. The second value may be generated using the third value.

With this configuration, a third value, which indicates prevalence of an infectious disease in an organization, is generated using a result of recognition of a sound performed by a sound recognition apparatus such as a smart speaker, and prevalence information and infection information reflect the third value.

In the above aspect, the evaluation result of the first evaluation may be output to a manager terminal owned by a manager of the group and the evaluation result of the second evaluation may be output to a guardian terminal owned by a guardian of the child.

With this configuration, a manager of a group can be notified of a child who is possibly infected with an infectious disease and take necessary measures to prevent prevalence of the infectious disease in the group. In addition, a guardian can be notified of an infection risk in the group, that is, a basis for determination whether to make the child attend the group can be provided.

In the above aspect, the evaluation result of the first evaluation may include temporal changes in the first infection risk value. The evaluation result of the second evaluation may include temporal changes in the second infection risk value.

With this configuration, temporal changes in the first infection risk value and temporal changes in the second infection risk value are output. Whether an infectious disease is spreading or being eradicated, therefore, can be presented.

In the above aspect, in the infection information, the first value may be obtained from a guardian terminal owned by a guardian of the child.

With this configuration, a terminal apparatus owned by a guardian inputs a first value, which indicates whether each of family members is infected with an infectious disease.

The above aspect may further include identifying the child whose first infection risk value is larger than the first reference value as a monitoring target child, detecting, using a camera installed in the children's facility, whether the monitoring target child has returned a toy to a toy storage, and spraying, if it is detected that the monitoring target child has returned a toy, a sterilization solution onto the toy from a sterilization apparatus.

With this configuration, when a toy used by a monitoring target child is returned to a toy storage, the toy is sterilized, Contact infection, therefore, can be prevented.

The present disclosure may also be implemented as a computer program for causing a computer to perform characteristic steps included in this method. It is needless to say that the computer program may be distributed through a non-transitory computer-readable storage medium, such as a CD-ROM, or a communication network such as the Internet.

Embodiments that will be described hereinafter are specific examples of the present disclosure. Values, shapes, components, steps, order of the steps, and the like mentioned in the following embodiments are example, and do not limit the present disclosure. Among the components described in the following embodiments, ones not described in the independent claims, which define the broadest concepts, will be described as optional components. Elements from different embodiments may be combined together.

First Embodiment

Embodiments of the present disclosure will be described hereinafter with reference to the drawings. FIG. 1 is a diagram illustrating an example of the overall configuration of an infection risk evaluation system according to a first embodiment of the present disclosure. The infection risk evaluation system is a system that evaluates an infection risk that a certain child whose infection risk is to be evaluated (hereinafter referred to as a "target child") is infected with an infectious disease and the target child's infection risk of being infected with the infectious disease in a class of a children's facility to which the target child belongs and that notifies a guardian and a manager of the children's facility of the infection risks.

An infectious disease refers to a disease caused by a pathogen that enters a living body and multiplies, such as influenza, dysentery, malaria, or norovirus.

A children's facility refers to a facility to which a target child belongs, such as a kindergarten, a nursery school, an elementary school, or a day nursery.

A child refers to a person who attends a children's facility, such as a child who goes to a kindergarten, a nursery school, or the like or a child who goes to an elementary school.

The infection risk evaluation system includes a server 10, a guardian terminal 20, a smart speaker 30 (an example of a sound recognition apparatus), a manager terminal 40, a camera 50, and a sterilization apparatus 60. The server 10 to the sterilization apparatus 60 are communicably connected to one another over a network NT. The network NT is achieved, for example, by public communication networks including a mobile phone communication network and an Internet communication network. In addition, an infection information server 70 that provides area infection information illustrated in FIG. 10 is connected to the network NT.

The server 10 is achieved by one or more computers and controls the entirety of the infection risk evaluation system.

The guardian terminal 20 is achieved, for example, by a personal computer installed in a house of a target child whose infection risk is to be evaluated or a mobile terminal owned by a guardian of a target child and transmits, to the server 10, family infection information (an example of infection information), which is information regarding a condition of infection with an infectious disease among family members of the target child. More specifically, the guardian terminal 20 includes a processor 201 that controls the entirety thereof, a display unit 202 that displays various images under the control of the processor 201, an operation unit 203 that receives operations performed by a guardian, and a communication unit 204 that transmits various pieces of data under the control of the processor 201. The operation unit 203 is, for example, an input device such as a touch panel, a keyboard, or a mouse.

Although FIG. 1 illustrates only one guardian terminal 20 for convenience of description, this is just an example. More than one guardian terminals 20 corresponding to more than one families may exist, instead.

The smart speaker 30 is installed in an organization to which each of the family members of the target child belongs and used for the server 10 to obtain prevalence information, which indicates a condition of prevalence of an infectious disease in the organization. More specifically, the smart speaker 30 includes a microphone 301 that collects sounds uttered in the organization, a processor 302 that recognizes the collected sounds, and a communication unit 303 that transmits, to the server 10, results (text data indicating the uttered sounds) of the recognition of the sounds performed by the communication unit 302. Furthermore, the smart speaker 30 is connected to the network NT and includes a speaker 304 that converts audio messages transmitted from an external server, which provides various services for an owner of the smart speaker 30, into sounds and that outputs the sounds.

Although the smart speaker 30 performs sound recognition using the processor 302 in the above description, the present disclosure is not limited to this. An external service may perform sound recognition, instead. In this case, the smart speaker 30 may transmit sound signals collected by the microphone 301 to the external server, receive results of recognition of sounds performed by the external server, and transmit the results to the server 10. The external server may be the server 10.

Here, the organization is, for example, a workplace to which a father or a mother of the target child belongs. Alternatively, the organization is, for example, a school, a kindergarten, or a nursery school to which an elder brother, a younger brother, an elder sister, or a younger sister, who is a family member of the target child, belongs. When the organization is a workplace, the smart speaker 30 is installed, for example, in a room of the workplace. When the organization is a school, the smart speaker 30 is installed, for example, in a classroom of the school.

Although FIG. 1 illustrates one smart speaker 30 for convenience of description, this is just an example. Smart speakers 30 are installed in a school to which an elder brother belongs, the workplace to which the father belongs, and a school to which a younger brother belongs. When there are entries of more than one families, smart speakers 30 are also installed in organizations to which family members of each of the families belong.

The manager terminal 40 is achieved by a personal computer installed in the children's facility to which the target child belongs or a mobile terminal owned by a manager (e.g., a class teacher) of a class to which the target child belongs. More specifically, the manager terminal 40 includes a processor 401 that controls the entirety thereof, a display unit 402 that displays various images under the control of the processor 401, an operation unit 403 that receives operations performed by the manager, and a communication unit 404 that transmits various pieces of data under the control of the processor 401.

The camera 50 is achieved, for example, by a camera that is installed in the children's facility to which the target child belongs and that has a communication function and used to monitor a monitoring target child whose infection risk is high in the children's facility. More specifically, the camera 50 includes a processor 501 that controls the entirety of the camera 50, an image sensor 502 such as a charge-coupled device (CCD) sensor or a complementary metal-oxide-semiconductor (CMOS) sensor, and a communication unit 503 that transmits, under the control of the processor 501, image data obtained by the image sensor 502.

The sterilization apparatus 60 is achieved, for example, by a sterilization apparatus that is installed in the children's facility to which the target child belongs and that has a communication function and sprays a sterilization solution, such as hypochlorous acid or alcohol, onto toys used by a monitoring target child. The camera 50 and the sterilization apparatus 60 will be described in detail later in a second embodiment.

The infection information server 70 is a server managed by a hospital, a medical association, or the like, for example, and, if an infectious disease becomes prevalent, provides area infection information, which indicates distribution of carriers in each area.

FIG. 2 is a block diagram illustrating an example of the configuration of the server 10 illustrated in FIG. 1. The server 10 includes a communication device 11, a processor 12, and a memory 13. The communication device 11 is a communication device for connecting the server 10 to the network NT. The processor 12 is achieved by a central processing unit (CPU), for example, and includes a first obtaining unit 121, a second obtaining unit 122, a first infection risk value calculation unit 123, a second infection risk value calculation unit 124, an evaluation unit 125, and an output unit 126. Here, the first obtaining unit 121 to the output unit 126 are achieved, for example, when the processor 12 executes an infection risk evaluation program, which is stored in the memory 13, for causing a computer to function as the server 10. The infection risk evaluation program may be downloaded from the network NT and provided for the market or stored in a non-transitory computer-readable storage medium and provided for the market.

The first obtaining unit 121 obtains, from the communication device 11, family infection information transmitted from the guardian terminal 20 and received by the communication device 11. The first obtaining unit 121 then stores the obtained family infection information in a family infection information DB (database) 132. Here, a guardian inputs, to the guardian terminal 20 at certain time intervals (e.g., every day), for example, information indicating whether some or all of family members are infected with an infectious disease and information indicating a name of the infectious disease. The guardian terminal 20 then generates family infection information including the information input by the guardian and transmits the family infection information to the server 10. The first obtaining unit 121 thus obtains family infection information at the certain time intervals. Here, the first obtaining unit 121 may refer to a table to which communication addresses of guardian terminals 20 and identifiers of guardians who own the guardian terminals 20 are registered in advance and determine family infection information regarding a family corresponding to the obtained family infection information.

The second obtaining unit 122 obtains organization infection information (an example of prevalence information), which is information regarding a condition of prevalence of an infectious disease in the organization to which each of the family members belongs. More specifically, the second obtaining unit 122 may obtain organization infection information by analyzing a result of recognition of a sound transmitted from the smart speaker 30 and received by the communication device 11.

If a result of recognition of a sound indicating prevalence of an infectious disease such as influenza is obtained from the smart speaker 30 installed in the school to which the elder brother belongs, for example, the second obtaining unit 122 obtains organization infection information indicating that the infectious disease is prevalent in the organization (school) to which the elder brother belongs and stores the organization infection information in an organization infection information DB 133. If a result of recognition of a sound indicating prevalence of an infectious disease such as influenza is obtained from the smart speaker 30 installed in the workplace to which the father belongs, for example, the second obtaining unit 122 obtains organization infection information indicating that the infectious disease is prevalent in the organization (workplace) to which the father belongs and stores the organization infection information in the organization infection information DB 133.

The second obtaining unit 122 thus determines, after a result of recognition of a sound is transmitted from the smart speaker 30, an organization in which the smart speaker 30 that has transmitted the result of recognition of a sound is installed. In this case, the second obtaining unit 122 refers to a table on which communication addresses of smart speakers 30 and places in which the smart speakers 30 are installed are associated with each other in advance and determines an organization in which the smart speaker 30 that has transmitted the result of recognition of a sound is installed. If the obtained result of recognition of a sound includes a word indicating an "infectious disease" (e.g., influenza or norovirus) and a word indicating prevalence of an infectious disease (e.g., prevalent), the second obtaining unit 122 may generate organization infection information indicating that the infectious disease is prevalent in the determined organization.

The first infection risk value calculation unit 123 calculates a first infection risk value using family infection information obtained by the first obtaining unit 121, organization infection information obtained by the second obtaining unit 122, and first infection risk coefficients.

Here, the first infection risk value is a value indicating a degree of an infection risk that the target child is infected with an infectious disease. The first infection risk coefficients are coefficients obtained by expressing infection risks between the target child and the family members in numbers. Details of calculation of the first infection risk value will be described later.

The second infection risk value calculation unit 124 calculates a second infection risk value using the first infection risk value. Here, the second infection risk value is a value indicating a degree of the target child's infection risk of being infected with an infectious disease in the class to which the target child belongs. Details of calculation of the second infection risk value will be described later.

The evaluation unit 125 performs first evaluation for evaluating an infection risk that the target child is infected with an infectious disease by comparing a first infection risk value calculated by the first infection risk value calculation unit 123 with a certain first reference value. If the first infection risk value is larger than the first reference value, for example, the evaluation unit 125 may determine in the first evaluation that the target child is infected with an infectious disease. If the first infection risk value is equal to or smaller than the first reference value, the evaluation unit 125 may determine in the first evaluation that the target child is not infected with an infectious disease.

In addition, the evaluation unit 125 performs second evaluation for evaluating the target child's infection risk of being infected with an infectious disease in the class to which the target child belongs by comparing a second infection risk value calculated by the second infection risk value calculation unit 124 with a certain second reference value. If the second infection risk value is larger than the second reference value, for example, the evaluation unit 125 may determine in the second evaluation that the target child is likely to be infected with an infectious disease in the class to which the target child belongs. If the second infection risk value is equal to or smaller than the second reference value, the evaluation unit 125 may determine in the second evaluation that the target child is not likely to be infected with an infectious disease in the class to which the target child belongs.

In the following description, the evaluation unit 125 performs both the first evaluation and the second evaluation. The present disclosure, however, is not limited to this. The evaluation unit 125 may perform at least either the first evaluation or the second evaluation.

The output unit 126 outputs a first evaluation result obtained as a result of the first evaluation and a second evaluation result obtained as a result of the second evaluation. For example, the output unit 126 may transmit, through the communication device 11, the first evaluation result to the manager terminal 40 owned by the manager of the class to which the target child belongs. The output unit 126 may transmit, through the communication device 11, the second evaluation result to the guardian terminal 20 owned by the guardian of the target child.

The memory 13 is achieved by a semiconductor memory, for example, and includes a family information DB 131, the family infection information DB 132, the organization infection information DB 133, and an infection risk coefficient DB 134.

FIG. 3 is a diagram illustrating an example of the data structure of the family information DB 131. Although FIG. 3 illustrates the family information DB 131 for one family, this is just an example. When there are entries of more than one families, there is a family information DB 131 for each of the more than one families.

In the family information DB 131, a family information table is assigned to each of the target child and the family members. In the example illustrated in FIG. 3, the family information DB 131 includes a family information table 131A for "A", who is the target child, and four family information tables 131B, 131C, 131D, and 131E corresponding to "father", "mother", "elder brother", and "younger brother", respectively, who are the family members of the target child.

The family information table 131A includes fields of "name", "nickname", "age", "class", "face", and "live with". The "name" field stores a name of the target child. The "nickname" field stores a nickname of the target child. The "age" field stores an age of the target child. The "face" field stores image data regarding a face of the target child. The "live with" field stores family members with whom the target child lives. Here, the "live with" field stores "father", "mother", "elder brother", and "younger brother".

The family information tables 131B to 131E each include fields of "relationship", "name", "nickname", "age", and "belonging". The "relationship" field stores a relationship with the target child. The "name", "nickname", and "age" fields are the same as on the family information table 131A. The "belonging" field stores an organization to which a family member belongs. Here, the organizations to which "father", "mother", "elder brother", and "younger brother" belong are "Matsushiba Electric", "housewife", "A elementary school", and "B nursery school", respectively.

FIG. 4 is a diagram illustrating an example of the data structure of the family infection information DB 132. Here, a family infection information DB 132 for the family illustrated in FIG. 3 is illustrated. When there are entries of more than one families, however, there is a family infection information DB 132 for each of the more than one families.

The family infection information DB 132 is a table created using family infection information obtained by the first obtaining unit 121 and organization infection information obtained by the second obtaining unit 122. The family infection information DB 132 stores, at certain time intervals (here, every day), information indicating whether each of the family members of the target child, namely "father", "mother", "elder brother", and "younger brother", is infected with an infectious disease and information indicating whether the infectious disease is prevalent in their respective organizations.

The family infection information DB 132 includes fields of "infection" and "belonging" for each family member. The "infection" field stores information indicating whether a family member is infected with an infectious disease. Here, "1" is stored if the family member is infected, and "0" is stored if the family member is not infected. "1" stored in the "infection" field is an example of a first value.

The "belonging" field stores information indicating whether an infectious disease is prevalent in an organization to which a family member belongs. Here, "1" is stored if an infectious disease is prevalent, and "0" is stored if an infectious disease is not prevalent. "1" stored in the "belonging" field is an example of a second value.

For example, "1" is stored in the "infection" field and "0" is stored in the "belonging" field of "father" today (Jan. 10, 2018). That is, it is indicated that "father" is infected with an infectious disease, but the infectious disease is not prevalent in his workplace.

In the example illustrated in FIG. 4, the guardian terminal 20 has transmitted family infection information indicating that the father and the younger brother are infected and the mother and the elder brother are not infected today, and the first obtaining unit 121 inputs "1" to the "infection" field of the father and the younger brother and "0" to the "infection" field of the mother and the elder brother.

In addition, "1" and "0" input to the "belonging" field illustrated in FIG. 4 reflect the organization infection information DB 133 illustrated in FIG. 5. For example, a reason why "1" is input to the "belonging" field of the elder brother illustrated in FIG. 4 today is that "1", which indicates prevalence of an infectious disease, is registered in a field of "A elementary school", to which the elder brother belongs, of the organization infection information today. The first obtaining unit 121 inputs "1" or "0" to the "belonging" field of the family infection information DB 132 while referring to the organization infection information DB 133 illustrated in FIG. 5. Here, when inputting information such as "1" or "0" to the family infection information DB 132 illustrated in FIG. 4, the first obtaining unit 121 may identify an organization to which each of the family members belongs by referring to the family information DB 131 illustrated in FIG. 3.

FIG. 5 is a diagram illustrating an example of the data structure of the organization infection information DB 133. The organization infection information DB 133 stores, at certain time intervals (here, every day), information indicating whether an infectious disease is prevalent for each of organizations whose entries exist. In the example illustrated in FIG. 5, information indicating whether an infectious disease is prevalent is stored for each of "A elementary school", "B nursery school", "Matsushiba Electric", and "Yokohama Trading", Here, "1" is stored if an infectious disease is prevalent, and "0" is stored if an infectious disease is not prevalent. "1" stored in a cell of the organization infection information DB 133 is an example of a third value.

For example, "1" is stored in the "A elementary school" field today. This is because a result of recognition of a sound transmitted today from a smart speaker 30 installed in the A elementary school includes an utterance indicating that an infectious disease is prevalent. The second obtaining unit 122, therefore, has input information "1", which indicates prevalence of an infectious disease, to the "A elementary school" field today.

"0" is stored in the "Matsushiba Electric" field today. This is because a result of recognition of a sound transmitted today from a smart speaker 30 installed in Matsushiba Electric does not include an utterance indicating prevalence of an infectious disease. The second obtaining unit 122, therefore, has not input the information "1", which indicates prevalence of an infectious disease, to the "Matsushiba Electric" field today. "0" is stored in each cell of the organization infection information DB 133 by default. "0", therefore, is stored in each cell unless the second obtaining unit 122 inputs "1" to the cell.

The family infection information DB 132 illustrated in FIG. 4 and the organization infection information DB 133 illustrated in FIG. 5 may be created for each type of infectious disease or may be created regardless of a type of infectious disease.

FIG. 6 is a diagram illustrating an example of the data structure of the infection risk coefficient DB 134. In FIG. 6, "RF" denotes the first infection risk coefficients, and "RM" denotes second infection risk coefficients. The first infection risk coefficients RF include an overall first infection risk coefficient and a first infection risk coefficient of each family member. The overall first infection risk coefficient is a value for determining a weight of the first infection risk coefficients RF, and "1" is used here. The first infection risk coefficient of each family member is a first infection risk coefficient RF between the target child and the family member. Within a range of "0" to "1", a larger value is assigned to a family member who is physically closer to the target child.

Here, "younger brother", "mother", "elder brother", and "father" are physically closer to the target child in this order, and the first infection risk coefficient of each family member decreases in this order. First infection risk coefficients RF for brothers are determined as follows on the assumption that brothers closer in age to the target child is physically closer to the target child. That is, when a difference in age between the target child and a brother is 1 year or smaller, the first infection risk coefficient RF for the brother is determined as "1", When a difference between the target child and a brother is larger than 1 year, on the other hand, the first infection risk coefficient RF for the brother is determined as "0.5".

The second infection risk coefficients RM, too, as with the first infection risk coefficients RF, include an overall second infection risk coefficient and a second infection risk coefficient of each family member. The overall second infection risk coefficient is a value for determining a weight of the second infection risk coefficients RM, and "0.3" is used here. A reason why the overall second infection risk coefficient is set lower than the overall first infection risk coefficient here is that whether the target child will be infected with an infectious disease is more greatly affected by whether the family members are infected with the infectious disease than whether the infectious disease is prevalent in the organizations to which the family members belong.

The second infection risk coefficient of each family member indicates a second infection risk coefficient RM between the target child and the family member and varies within a range of "0" to "1". With respect to the second infection risk coefficient of each family member, the second infection risk coefficients of the elder and younger brothers are higher than those of the father and the mother on the assumption that children are more susceptible to secondary infection than adults.

First Infection Risk Values

Next, a specific example of calculation of first infection risk values performed by the first infection risk value calculation unit 123 will be described. FIG. 7 is a table used to describe the specific example of the first infection risk values. The table illustrated in FIG. 7 is obtained by extracting today's family infection information illustrated in FIG. 4. In FIG. 7, DF denotes information indicating whether each of the family members, namely the father, the mother, the elder brother, and the younger brother, is infected with an infectious disease, and DM denotes information indicating whether an infectious disease is prevalent in the organization to which each of the family members, namely the father, the mother, the elder brother, and the younger brother, belongs.

Here, a first infection risk value today is denoted by Ro, a first infection risk value yesterday is denoted by R-1, a first infection risk value two days ago is denoted by R-2, and a first infection risk value n days ago is denoted by R-n.

The first infection risk value Ro is represented by a following expression (1).

$$Ro = \text{Family risk value } AF + \text{Organization risk value } AM \quad (1)$$

The family risk value AF is represented by a following expression (2).

$$AF = 1 \cdot \Sigma RF(c) \cdot DF(c) \quad (2)$$

Here, c denotes an index indicating a relationship between the target child and each of the one or more family members. For example, $RF(c) \cdot DF(c)$ of the target child's father is expressed as $RF(\text{father}) \cdot DF(\text{father})$, and $RF(c) \cdot DF(c)$ of the target child's elder brother is expressed as $RF(\text{elder brother}) \cdot DF(\text{elder brother})$. The expression $\Sigma RF(c) \cdot DF(c)$ indicates that $RF(c) \cdot DF(c)$ is calculated for each of the one or more family members, and $RF(c) \cdot DF(c)$ calculated for all the family members are added up. "1" at a top of a right side of expression (2) indicates the overall first infection risk coefficient. Expression (2) is an example of a first sum of first products of the first value and the first infection risk coefficients corresponding to the first value for all the family members.

The organization risk value AM is represented by expression (3).

$$AM = 0.3 \cdot \Sigma RM(c) \cdot DM(c) \quad (3)$$

"0.3" at a top of a right side of expression (3) indicates the overall second infection risk coefficient. Expression (3) is an example of a second sum of second products of the second value and the second infection risk coefficients corresponding to the second value for all the family members.

In the example illustrated in FIG. 7, expression (2) is converted into a following expression (4).

$$AF = 1 \cdot (RF(\text{father}) \cdot DF(\text{father}) + RF(\text{mother}) \cdot DF(\text{mother}) + RF(\text{elder brother}) \cdot DF(\text{elder brother}) + RF(\text{younger brother}) \cdot DF(\text{younger brother})) \quad (4)$$

Values in FIGS. 6 and 7 are substituted into expression (4), and the family risk value AF is obtained as follows.

$$AF = 1 \times (0.3 \cdot 1 + 0.8 \cdot 0 + 0.5 \cdot 0 + 1.1) = 1.3$$

In the example illustrated in FIG. 7, expression (3) is converted into a following expression (5).

$$AM = 0.3 \cdot (RM(\text{father}) \cdot DM(\text{father}) + RM(\text{mother}) \cdot DM(\text{mother}) + RM(\text{elder brother}) \cdot DM(\text{elder brother}) + RM(\text{younger brother}) \cdot DM(\text{younger brother})) \quad (5)$$

The values illustrated in FIGS. 6 and 7 are substituted into expression (5), and the organization risk value AM is obtained as follows.

$$AM = 0.3 \cdot (0.1 \cdot 0 + 0.1 \cdot 0 + 0.5 \cdot 1 + 1.1) = 0.45$$

The first infection risk value Ro, therefore, is obtained as 1.3+0.45=1.75.

The first infection risk value calculation unit 123 thus calculates first infection risk values from n days ago to today by calculating a first infection risk value every day. The calculated first infection risk values are stored in the memory 13 while being associated with an identifier of the target child.

The first infection risk value calculation unit 123 also calculates first infection risk values while determining, as target children, children in a target class to which the target child belongs and stores the first infection risk values in the memory 13 while associating the first infection risk values with identifiers of the target children. As a result, temporal changes in the first infection risk value of each child belonging to the target class are calculated and stored in the memory 13.

Second Infection Risk Values

Next, a specific example of calculation of second infection risk values performed by the second infection risk value calculation unit 124 will be described.

The second infection risk value calculation unit 124 calculates a second infection risk value by calculating, every day, the sum, or an average of the sum, of first infection risk values calculated for each of the children belonging to the target class as described above.

More specifically, the second infection risk value is calculated using a following expression (6).

$$\text{Second infection risk value} = \Sigma Ro(k) \qquad (6)$$

Here, Ro(k) denotes todays first infection risk value of a child k belonging to a target class, $\Sigma Ro(k)$ indicates that first infection risk values for children belonging to the target class are added up. The children and the first infection risk values are in one-to-one correspondence.

Alternatively, the second infection risk value may be calculated using a following expression (7).

$$\text{Second infection risk value} = (1/N) \cdot \Sigma Ro(k) \qquad (7)$$

Here, N denotes the number of children belonging to the target class.

If there are entries of classes other than the target class, the second infection risk value calculation unit 124 also calculates second infection risk values for the other classes while determining the other classes as target classes. The calculated second infection risk values are stored in the memory 13 while being associated with identifiers of the classes.

A second infection risk value for each class is thus calculated and accumulated in the memory 13 every day.

When an infection risk is compared between classes, second infection risk values may be calculated using expression (7), that is, average values.

Correction of First Infection Risk Values

Next, correction of first infection risk values performed by the first infection risk value calculation unit 123 will be described. When a first infection risk value tends to increase, the first infection risk value may be increased through correction, and when a first infection risk value tends to decrease, the first infection risk value may be decreased through correction.

More specifically, the first infection risk value Ro is corrected as in expression (8) when a corrected first infection risk value is denoted by Rop.

$$\text{When } Ro-(R-1) \leq 0, Rop = Ro+1$$

$$\text{When } Ro-(R-1)<0, Rop = Ro-0.2 \qquad (8)$$

That is, when the first infection risk value Ro is larger than yesterday, 1 is added. When the first infection risk value Ro is smaller than yesterday, 0.2 is subtracted.

Although a mode in which a fixed value "1" is added and a fixed value "0.2" is subtracted has been described above, this is just an example. Values other than "1" and "0.2" may be used as fixed values, instead.

When the first infection risk value Ro can be represented by a function f(x), the first infection risk value Ro may be corrected using a following expression (9).

$$\text{When } f(0) \leq 0, Rop = Ro+1$$

$$\text{When } f(0)<0, Rop = Ro-0.2 \qquad (9)$$

x denotes a factor for identifying a date, and x=0 indicates today. f(0), therefore, equals Ro.

By correcting the first infection risk value in this manner, an appropriate first infection risk value can be calculated while taking into consideration whether an infectious disease is spreading or being eradicated.

Alternatively, the second infection risk value may be calculated using a corrected first infection risk value.

In this case, the second infection risk value is represented by a following expression (10), which is obtained by replacing Ro(k) in expression (6) with Rop(k), or a following expression (11), which is obtained by replacing Ro(k) in expression (7) with Rop(k).

$$\text{Second infection risk value} = \Sigma Rop(k) \qquad (10)$$

$$\text{Second infection risk value} = (1/N) \cdot \Sigma Rop(k) \qquad (11)$$

Process

Figure 8:
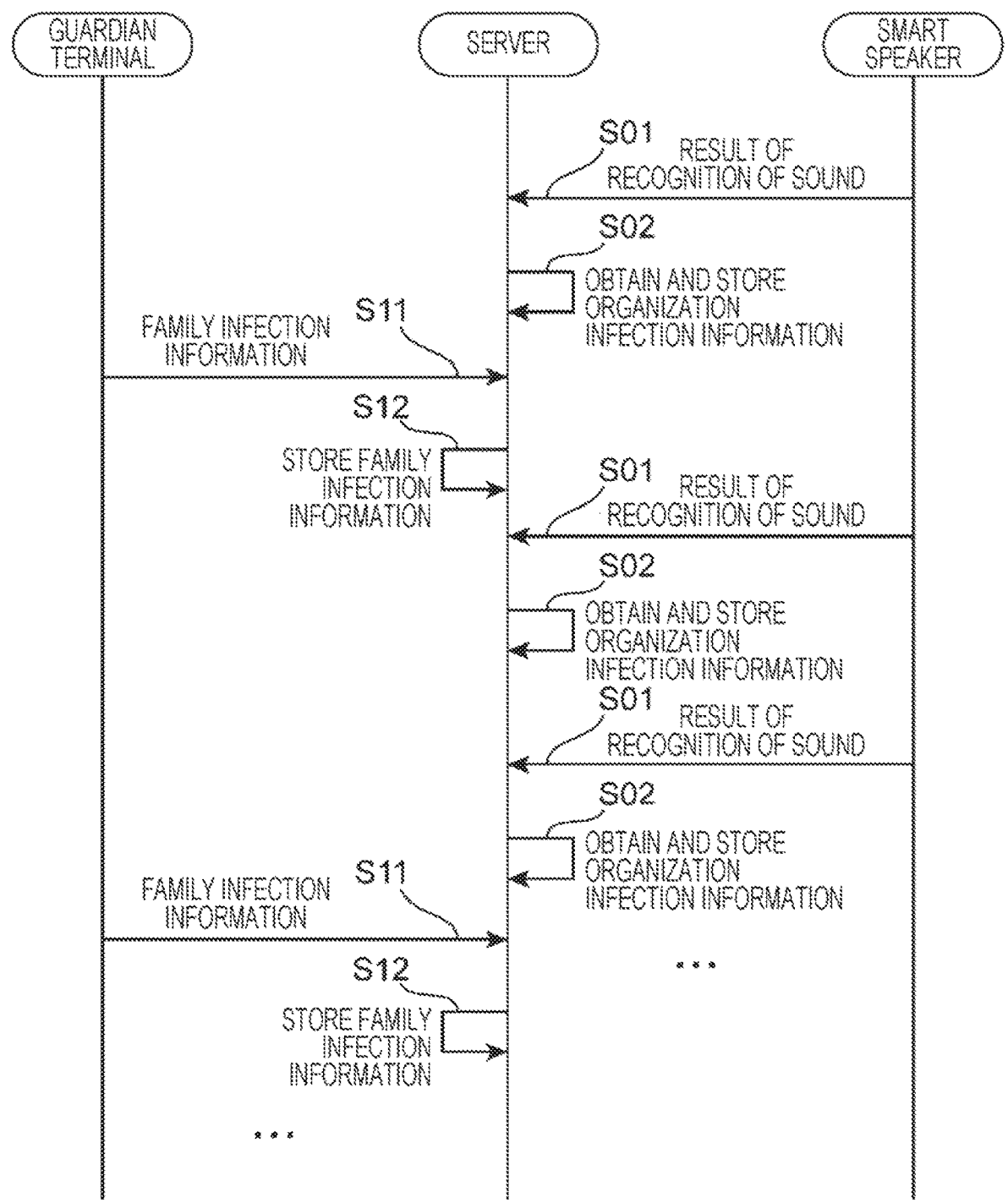
FIG. 8 is a sequence diagram illustrating an example of a process performed by the infection risk evaluation system in the present disclosure to obtain family infection information and organization infection information.

Next, a process performed by the infection risk evaluation system in the present disclosure will be described. FIG. 8 is a sequence diagram illustrating an example of a process performed by the infection risk evaluation system in the present disclosure to obtain family infection information and organization infection information.

Each time the smart speaker 30 collects a sound and generates a result of recognition of the sound, the smart speaker 30 transmits the result of recognition of the sound to the server 10 (S01). The communication device 11 of the server 10 receives the result of recognition of the sound, and the second obtaining unit 122 analyzes the result of recognition of the sound to obtain organization infection information and stores the organization infection information in the organization infection information DB 133 (S02). When a result of recognition of a sound indicating prevalence of an infectious disease is obtained from the smart speaker 30 installed in the A elementary school, for example, the second obtaining unit 122 inputs "1" to today's cell of the A elementary school to store organization infection information.

By repeating the above process, organization infection information is accumulated in the organization infection information DB 133.

The guardian terminal 20 receives, from the guardian, information indicating whether some or all of the family members are infected with an infectious disease and information indicating a name of the infectious disease, generates family infection information including these piece of information, and transmits the family infection information to the server 10 (S11).

The communication device 11 of the server 10 receives the family infection information, and the first obtaining unit 121 identifies a family corresponding to the family infection information from a communication address of the guardian terminal 20, and stores the family infection information in the family infection information DB 132 of the identified family (S12). When family infection information indicating that the father and the younger brother are infected is transmitted, for example, the first obtaining unit 121 inputs "1" to the "infection" field of the father and the younger brother in the family infection information DB 132 to store the family infection information.

The above process is repeated at certain time intervals (here, every day) to accumulate family infection information in the family infection information DB 132. Each time "1" is input to the organization infection information DB 133, the first obtaining unit 121 inputs the information to the "belonging" field of a corresponding family member in the family infection information DB 132. When "1" is input to today's cell of the A elementary school, for example, the first obtaining unit 121 refers to the family information DB 131 and identifies "elder brother", who belongs to the A elementary school, and inputs "1" to the "belonging" field of "elder brother" identified in the family infection information DB 132, As a result, the "belonging" field of the family infection information DB 132 reflects organization infection information.

Figure 9:
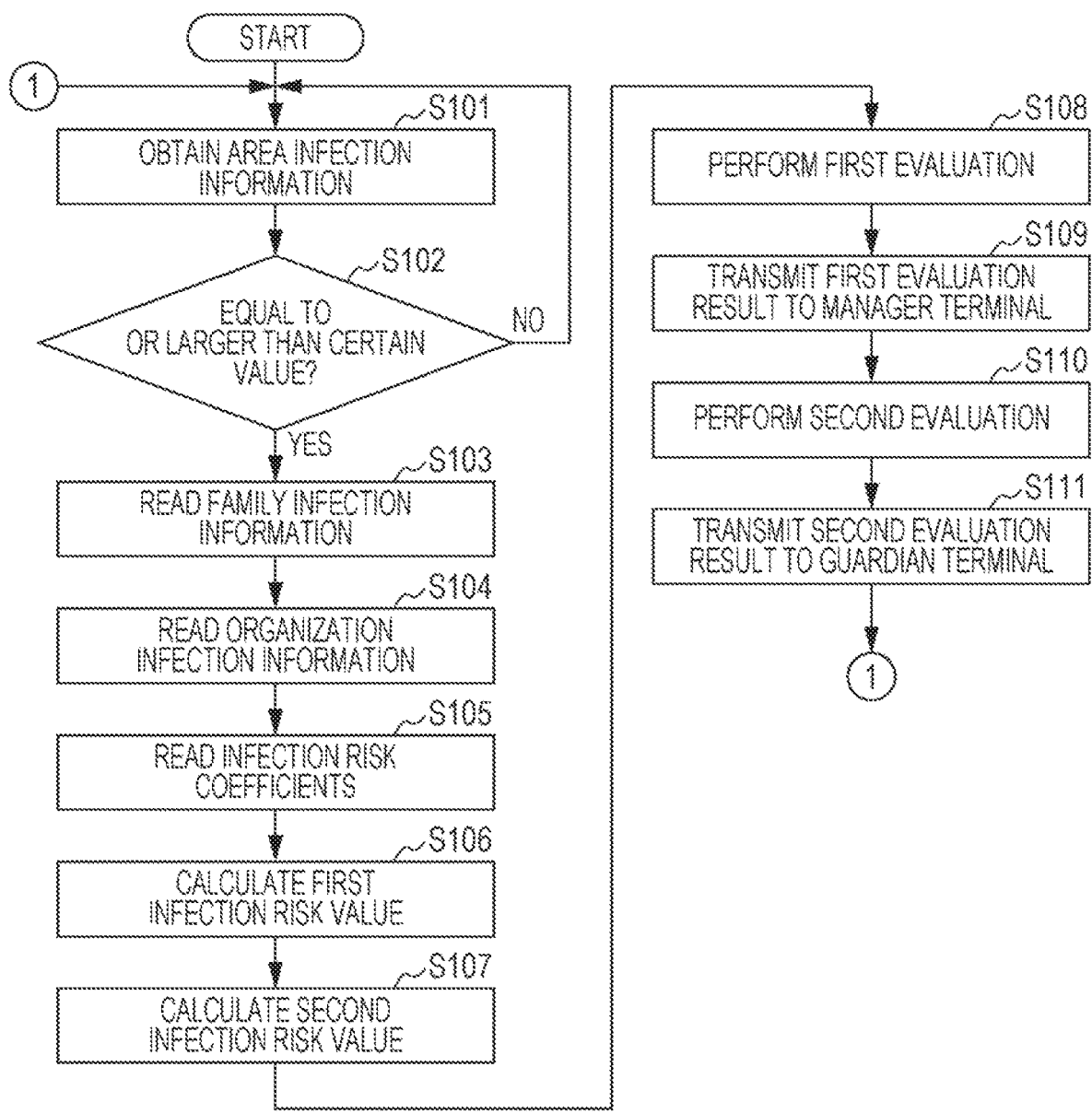
FIG. 9 is a flowchart illustrating an example of a process performed by the server of the infection risk evaluation system in the present disclosure.

FIG. 9 is a flowchart illustrating an example of a process performed by the server 10 of the infection risk evaluation system in the present disclosure. In FIG. 9, the process is performed for the family illustrated in FIG. 3 as an example. In S101, the communication device 11 receives area infection information from the infection information server 70. FIG. 10 is a diagram illustrating an example of the data structure of the area infection information. The area infection information is created for each infectious disease.

The area infection information is a table whose horizontal axis represents an area and whose vertical axis represents a period, and indicates the number of persons infected with an infectious disease in each area for every week. The area infection information is presented by a medical association that collects the number of patients diagnosed with an infectious disease at hospitals in each area. An area set along the horizontal axis in FIG. 10 is, for example, a city, a town, or a village. In FIG. 10, an area including at least a house in which the target child lives and the children's facility and areas adjacent to the area are set along the horizontal axis. The area infection information may be regularly presented throughout the year or may be regularly presented in a period in which an infectious disease becomes prevalent.

FIG. 9 is referred to again. In S102, if the number of persons infected included in the area infection information is equal to or larger than a certain value (YES in S102), the processor 12 causes the process to proceed to S103. If the number of persons infected is smaller than the certain value (NO in S102), the processor 12 causes the process to return to S101. That is, a flow illustrated in FIG. 9 is a flow in which a process in S103 and the later steps is performed if the number of persons infected in an area exceeds the certain value, and a processing load is reduced compared to a flow in which the process in S103 and the later steps is regularly performed.

For example, the processor 12 refers to the area infection information and, if the number of persons infected in at least one area is equal to or larger than the certain value in a period to which today belongs, determines a result of S102 as YES. The certain value depends on the population of an area and may be, for example, 5, 10, or 20.

In S103, the first infection risk value calculation unit 123 reads today's family infection information from the family infection information DB 132. In the example illustrated in FIG. 4, information "1" or "0" is read from the "infection" field of the father, the mother, the elder brother, and the younger brother.

In S104, the first infection risk value calculation unit 123 reads, from the organization infection information DB 133, organization infection information regarding the father, the mother, the elder brother, and the younger brother. In the example illustrated in FIG. 5, organization infection information regarding Matsushiba Electric, to which the father belongs, the A elementary school, to which the elder brother belongs, and the B nursery school, to which the younger brother belongs, is read. Although organization infection information is read from the organization infection information DB 133 here, this is just an example. Since the "belonging" field of the family infection information DB 132 reflects organization infection information, the first infection risk value calculation unit 123 may, in S104, read the organization infection information by reading information "1" or "0" from the "belonging" field of the family infection information DB 132.

In S105, the first infection risk value calculation unit 123 reads infection risk coefficients from the infection risk coefficient DB 134. Here, the various infection risk coefficients illustrated in FIG. 6 are read.

In S106, the first infection risk value calculation unit 123 calculates a first infection risk value of the target child using the family infection information read in S103, the organization infection information read in S104, and the various infection risk coefficients read in S105. Here, calculation is performed using the above expression (1) to obtain the first infection risk value Ro.

In S107, the second infection risk value calculation unit 124 calculates a second infection risk value by substituting the first infection risk value calculated in S106 and first infection risk values for other children, read from the memory 13, at the children's facility to which the target child belongs into the above expression (6) or (7) to calculate the second infection risk value.

In S108, the evaluation unit 125 compares the first infection risk value calculated in S106 with the first reference value to perform the first evaluation and obtain a first evaluation result. Here, if the first infection risk value is larger than the first reference value, a first evaluation result indicating that the target child's infection risk is "high" is obtained, and if the first infection risk value is equal to or smaller than the first reference value, a first evaluation result indicating that the target child's infection risk is "low" is obtained.

There may be more than one first reference values. When two first reference values are denoted by TH1 and TH2 (>TH1), for example, the first evaluation result may indicate "high", "medium", and "low" if the first infection risk value is larger than TH2, within a range of TH1 to TH2, and smaller than TH1, respectively. In addition, since the first infection risk value becomes larger as the number of family members increases as indicated in expression (1), a value normalized such that a maximum value becomes 1 may be used in order to minimize variation due to the number of family members. In this case, TH1, which is one of the two thresholds for the first infection risk value, may be, say, 0.3, and TH2, which is the other threshold for the first infection risk value, may be, say, 0.7.

In S109, the output unit 126 transmits, through the communication device 11, the first evaluation result to the manager terminal 40 at the target class to which the target child belongs, Here, the first evaluation result is transmitted to the manager terminal 40 in order to make the manger take a necessary action to prevent the target child whose infection risk is high from infecting the other children with an infectious disease at the children's facility. This, however, is just an example, and the first evaluation result may be transmitted to the guardian terminal 20 owned by the guardian of the target child. As a result, the guardian of the target child can recognize that the target child is infected with the infectious disease and make the target child leave the children's facility early or stay away from the children's facility for a while. In S109, a mode in which the first evaluation result is output if the first evaluation result is "high" may be employed, instead.

In S110, the evaluation unit 125 compares the second infection risk value calculated in S107 with the second reference value to perform the second evaluation for evaluating the target child's infection risk of being infected in the class to which the target child belongs and obtain a second evaluation result. Here, if the second infection risk value is larger than the second reference value, a second evaluation result indicating that the target child's infection risk at the target class is "high" is obtained, and if the second infection risk value is equal to or smaller than the second reference value, a second evaluation result indicating that the target child's infection risk at the target class is "low" is obtained.

As with the first reference value, there may be more than one second reference values. In this case, as in the case of the first evaluation result, the second evaluation result of one of three or more categories, namely "high", "medium", and "low", for example, is obtained. When two second reference values are denoted by TH3 and TH4 (>TH3), for example, TH3 may be, say, 0.3, and TH4 may be, say, 0.7.

In S111, the output unit 126 transmits, through the communication device 11, the second evaluation result to the guardian terminal 20 owned by the guardian of the target child. Here, the second evaluation result is transmitted to the guardian terminal 20 in order to provide a basis for determination for the guardian to determine whether to make the target child stay away from the children's facility and prevent the target child from being infected with an infectious disease at the children's facility. This, however, is just an example, and the second evaluation result may be transmitted to the manager terminal 40 owned by the manager of the class to which the target child belongs, instead. As a result, the manger can determine whether to temporarily close the target class. In S111, a mode in which the second evaluation result is output if the second evaluation result is "high" may be employed, instead. After processing in S111 ends, the process returns to S101.

Display Screen

Figure 11:
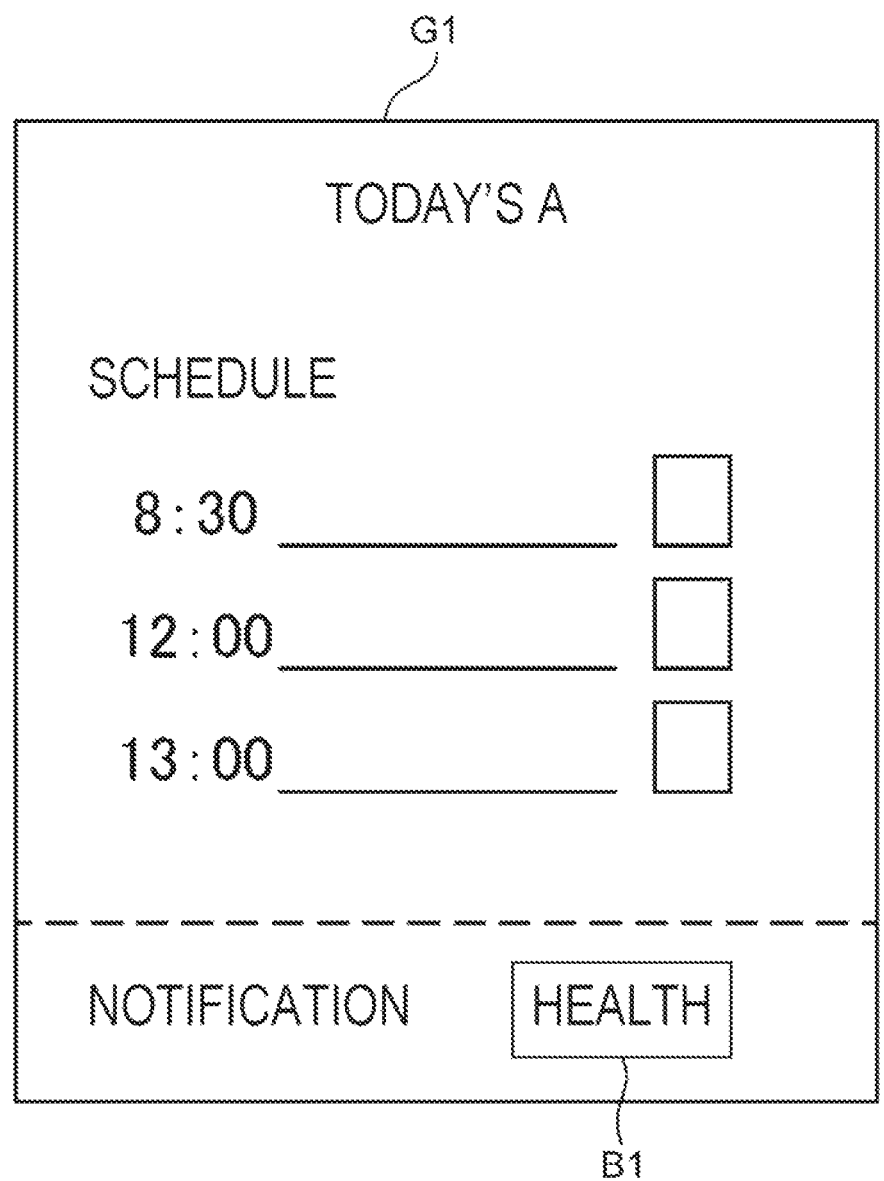
FIG. 11 is a diagram illustrating a first display screen displayed on a guardian terminal.

FIG. 11 is a diagram illustrating an example of a first display screen G1 displayed on the guardian terminal 20. The first display screen G1 is a screen for displaying notifications from the children's facility to which the target child belongs. Here, the first display screen G1 displays a schedule of the target child on the day at the children's facility as a list. A health button B1 indicating "health" is displayed in a lower part of the first display screen G1. When the guardian inputs an operation for selecting (e.g., tapping) the health button B1 and the operation unit 203 receives the operation, the processor 201 displays a second display screen G2 illustrated in FIG. 12 on the display unit 202.

Figure 12:
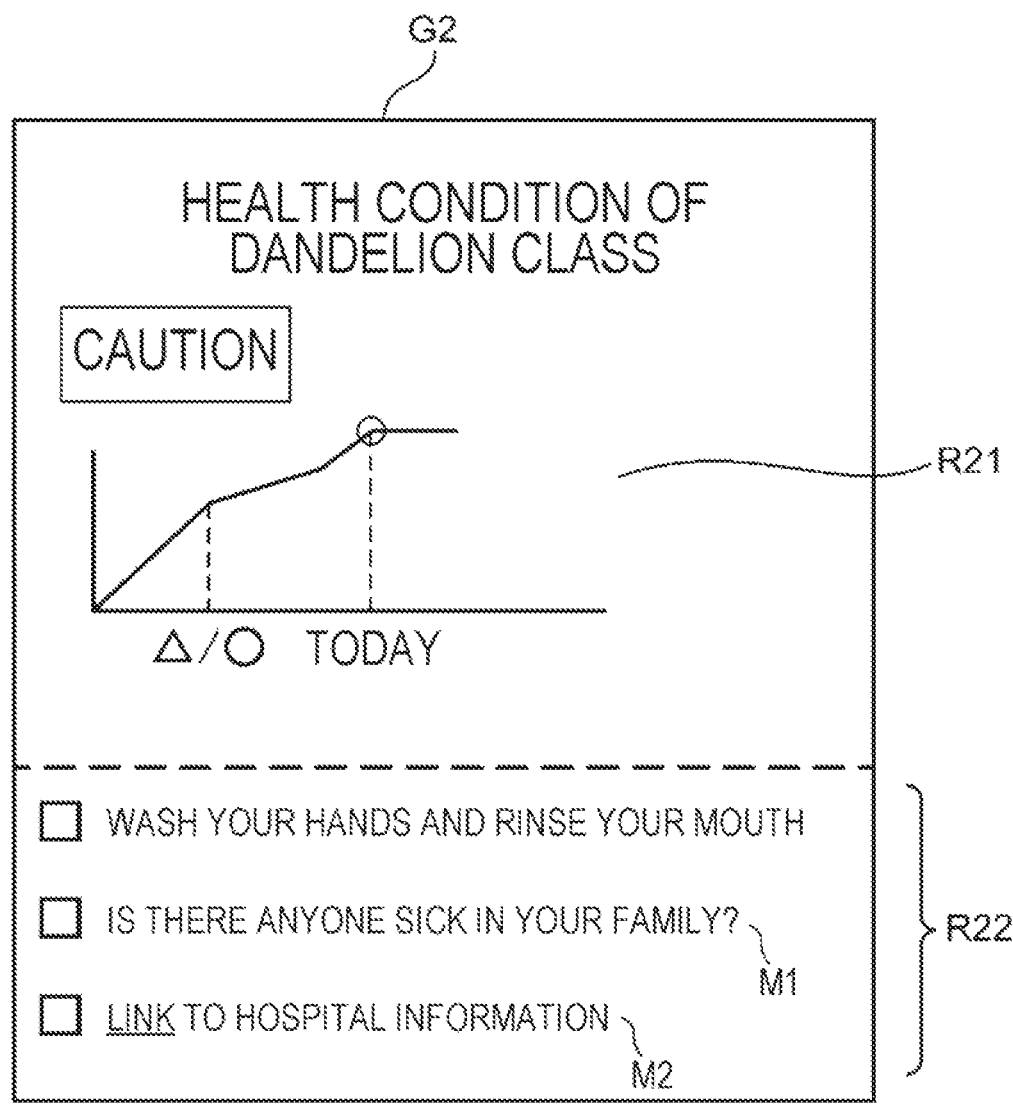
FIG. 12 is a diagram illustrating an example of a second display screen displayed on the guardian terminal.

FIG. 12 is a diagram illustrating an example of the second display screen G2 displayed on the guardian terminal 20. The second display screen G2 includes a graph display field R21 in which a health condition of a dandelion class, to which the target child belongs, is displayed as a graph. In the graph display field R21, a graph indicating temporal changes in the second infection risk value by representing the second infection risk value with a vertical axis thereof and the date with a horizontal axis thereof is displayed. Because a second evaluation result is "high" today in this graph, a message, "Caution", is displayed.

An advice display field R22 is displayed under the graph display field R21, In the advice display field R22, a precaution against an infectious disease at home, namely "Wash your hands and rinse your mouth", is displayed. In the advice display field R22, a message M1, "It there anyone sick in your family?", is also displayed. When the guardian inputs an operation for selecting the message M1 and the operation unit 203 receives the operation, the processor 201 displays a third display screen G3 illustrated in FIG. 13 on the display unit 202.

Figure 13:
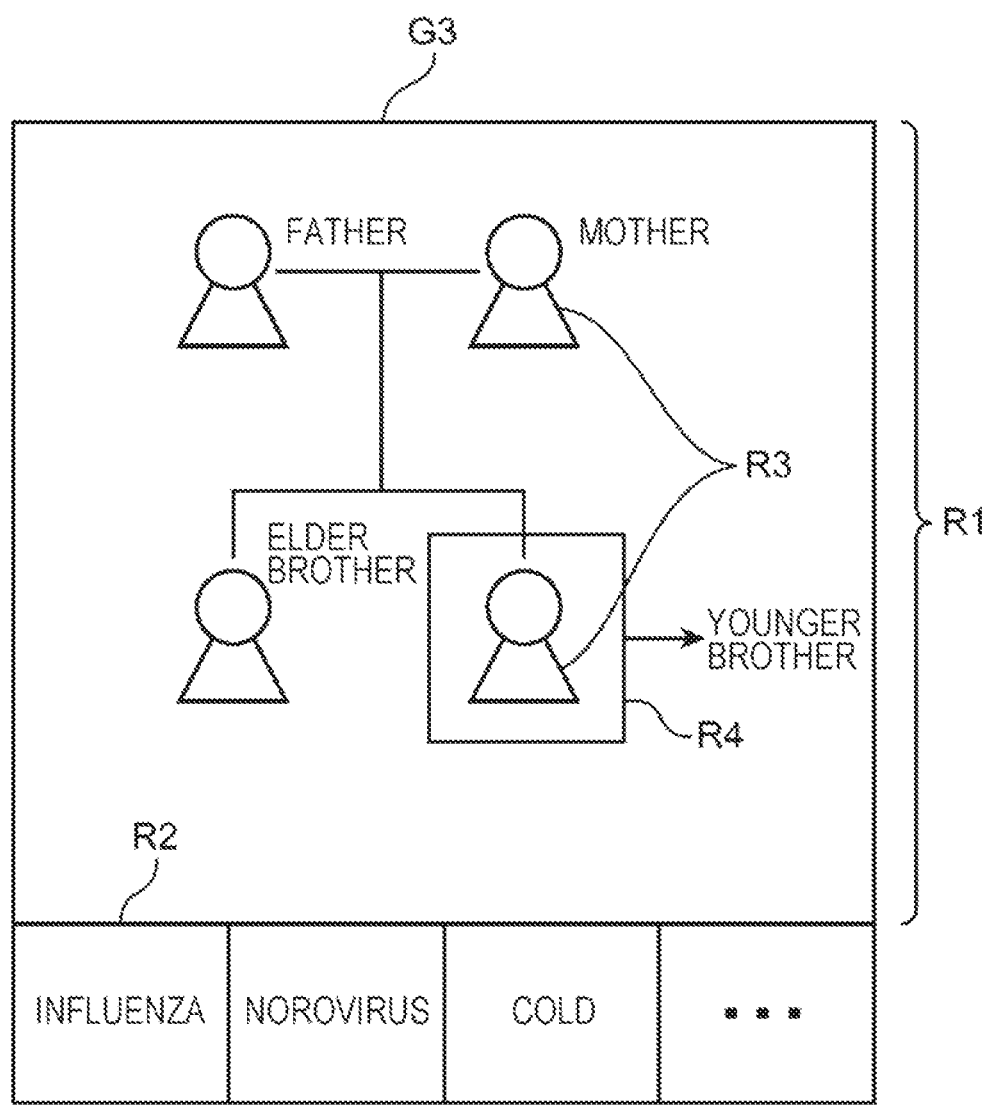
FIG. 13 is a diagram illustrating an example of a third display screen displayed on the guardian terminal.

FIG. 13 is a diagram illustrating an example of the third display screen G3 displayed on the guardian terminal 20. The third display screen G3 is a screen for inputting information indicating whether each of the family members is infected with an infectious disease.

The third display screen G3 includes a main screen R1 in which relationships between the family members are displayed as a tree and a disease name input button R2 displayed under the main screen R1. In the main screen R1, icons R3 indicating the family members are displayed. Here, four icons R3 corresponding to the father, the mother, the elder brother, and the younger brother other than the target child are displayed.

The disease name input button R2 is a button for inputting a name of a disease for the family members. Here, disease input buttons R2 corresponding to names of diseases such as "influenza", "norovirus", and "cold" are displayed.

When the guardian inputs an operation for selecting a desired family member and the operation unit 203 receives the operation, the processor 201 moves a cursor R4 to an icon R3 corresponding to the family member. When the guardian selects one of the disease input buttons R2, the operation unit 203 receives a name of a disease for the selected family member. The processor 201 transmits the received name of a disease to the server 10 through the communication unit 204 while associating the received name of a disease with an identifier of the selected family member. As a result, the server 10 obtains family infection information.

FIG. 12 is referred to again. A message M2, "Link to hospital information", is also displayed in the advice display field R22. When the guardian inputs an operation for selecting a "Link" part of the message M2 and the operation unit 203 receives the operation, the processor 201 displays a fourth display screen G4 illustrated in FIG. 14.

Figure 14:
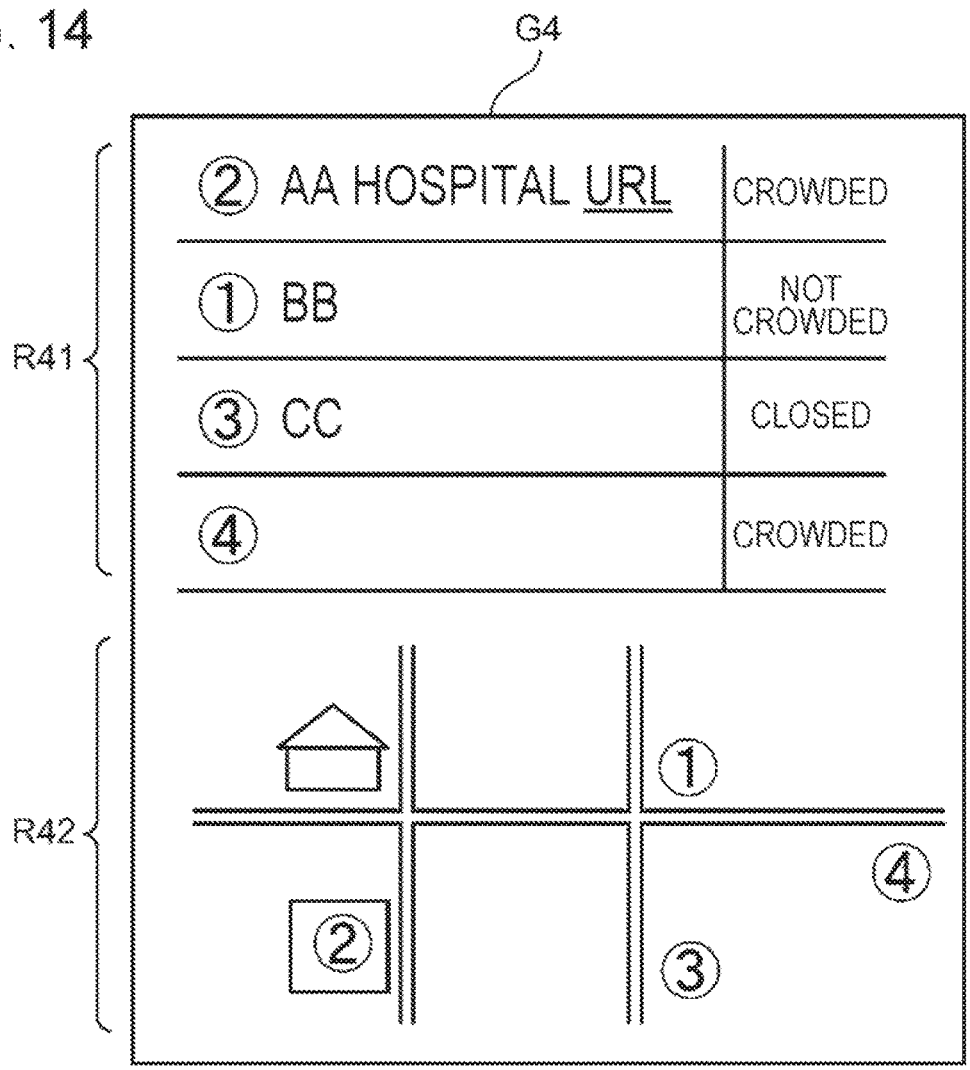
FIG. 14 is a diagram illustrating an example of a fourth display screen displayed on the guardian terminal.

FIG. 14 is a diagram illustrating an example of the fourth display screen G4 displayed on the guardian terminal 20. The fourth display screen G4 is a screen for displaying hospitals closest to the target child as a list. The fourth display screen G4 includes a list display field R41 for displaying closest hospitals as a list. In the list display field R41, identification numbers of the closest hospitals, names of the hospitals, uniform resource locators (URLs), and crowding conditions are associated with one another.

Since the crowding conditions are displayed in the list display field R41, the guardian can easily determine a hospital to be selected. When the guardian inputs an operation for selecting a URL part of the list display field R41 and the operation unit 203 receives the operation, the processor 201 displays a website of a corresponding hospital on the display unit 202.

An access map display field R42 indicating an access map to the hospitals displayed in the list display field R41 as a list is displayed under the list display field R41. In the access map display field R42, the identification numbers of the hospitals are displayed in the list display field R41 at positions of the hospitals displayed as a list. The guardian, therefore, can easily recognize places of the hospitals displayed in the list display field R41 as a list.

Figure 15:
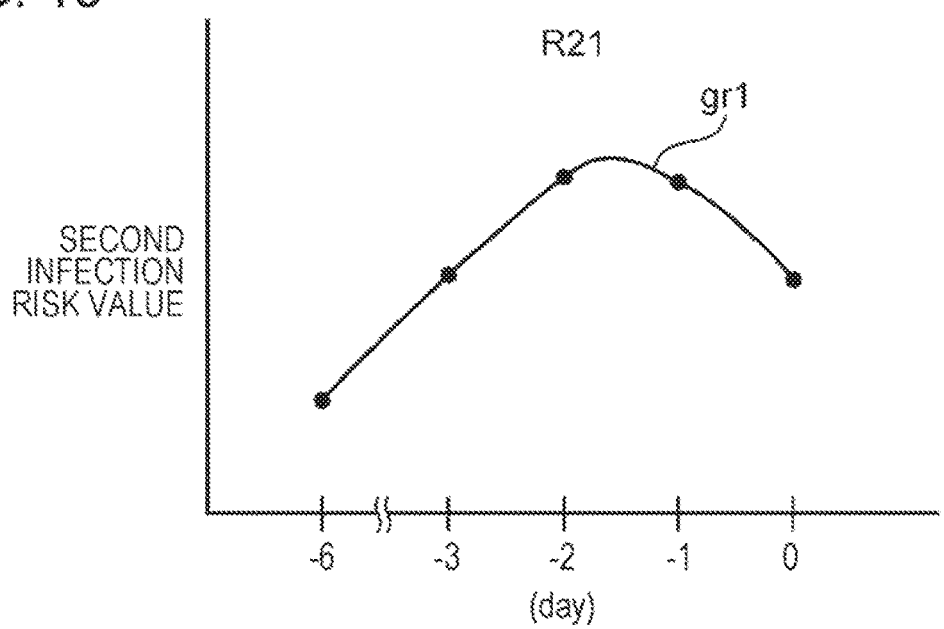
FIG. 15 is a diagram in which a graph display field illustrated in FIG. 12 is expanded.

FIG. 15 is a diagram in which the graph display field R21 illustrated in FIG. 12 is expanded. As illustrated in FIG. 15, a graph gr1 indicating temporal changes in the second infection risk value by representing the second infection risk value with a vertical axis thereof is displayed in the graph display field R21. 0 on a horizontal axis indicates today, and −1 indicates yesterday, Here, −6 to 0 are provided for the graph gr1, and temporal changes in the second infection risk value from six days ago to today are illustrated.

Since the graph gr1 indicates temporal changes in the second infection risk value from several days ago to today, the guardian can check whether an infectious disease is spreading or being eradicated in the target class. The guardian, therefore, can easily determine whether to make the target child attend the class today. In the example illustrated in FIG. 15, the second infection risk value was increasing from six days ago to two days ago, but began to decrease two days ago. It can be seen that the second infection risk value is decreasing today.

Although the oldest second infection risk value displayed here is from six days ago, this is just an example. The oldest second infection risk value displayed may be from seven or more days ago or five or fewer days ago, instead.

Although the second infection risk value is displayed in FIG. 15, the first infection risk value may be displayed, instead. The graph gr1 illustrated in FIG. 15 may be displayed on the guardian terminal 20 and the manager terminal 40. In this case, the manager terminal 40 may display at least either a graph gr1 indicating the first infection risk value or a graph gr1 indicating the second infection risk value.

According to the first embodiment, the first infection risk value is calculated using not only family infection information regarding the target child but also organization infection information and the first infection risk coefficients between the target child and the family members. An infection risk that the target child is infected with an infectious disease, therefore, can be accurately estimated.

In addition, the second infection risk value is calculated using the first infection risk value. The child's infection risk of being infected at the target class to which the child belongs can be accurately estimated.

In addition, since the first evaluation result and the second evaluation result are output, the manager of the target class who has seen the first evaluation result can suppress prevalence of an infectious disease in the target class by, for example, preventing a child whose infection risk is high from becoming physically close to other children or asking a child whose infection risk is high not to attend the class.

In addition, the guardian who has seen the second evaluation result can prevent the target child from being infected with an infectious disease by, for example, making the target child stay away from the class.

The second infection risk value may be determined for each child as follows.

When the number of children in a class is denoted by n, a first infection risk value of a first child may be Ro(1), . . . , a first infection risk value of a k-th child may be Ro(k), . . . , a first infection risk value of an nth child may be Ro(n), a second infection risk value of the first child may be (Ro(2)+ . . . +Ro(k)+ . . . +Ro(n)), . . . , a second infection risk value of the k-th child may be (Ro(1)+ . . . +Ro(k−2)+Ro(k−1)+Ro(k+1)+Ro(k+2)+ . . . +Ro(n)), . . . , and a second infection risk value of the n-th child may be (Ro(1)+ . . . +Ro(k)+ . . . +Ro(n−1)). The second infection risk value of the first child may be (Ro(2)+ . . . +Ro(k)+ . . . +Ro(n))/(n−1), . . . , the second infection risk value of the k-th child may be (Ro(1)+ . . . +Ro(k−2)+Ro(k−1)+Ro(k+1)+Ro(k+2)+ . . . +Ro(n))/(n−1), and the second infection risk value of the n-th child may be (Ro(1)+ . . . +Ro(k)+ . . . +Ro(n−1))/(n−1), (Ro(1)+ . . . +Ro(k−2)+Ro(k−1)+Ro(k+1)+Ro(k+2)+ . . . +Ro(n)) may be expressed as (Ro(1) . . . +Ro(k) . . . +Ro(n)−Ro(k)).

Second Embodiment

In the second embodiment, when a monitoring target child whose first infection risk value is larger than the first reference value returns a toy to a toy storage in a children's facility, the toy is sterilized. In the second embodiment, the same components as in the first embodiment are given the same reference numerals, and description thereof is omitted.

Figure 16:
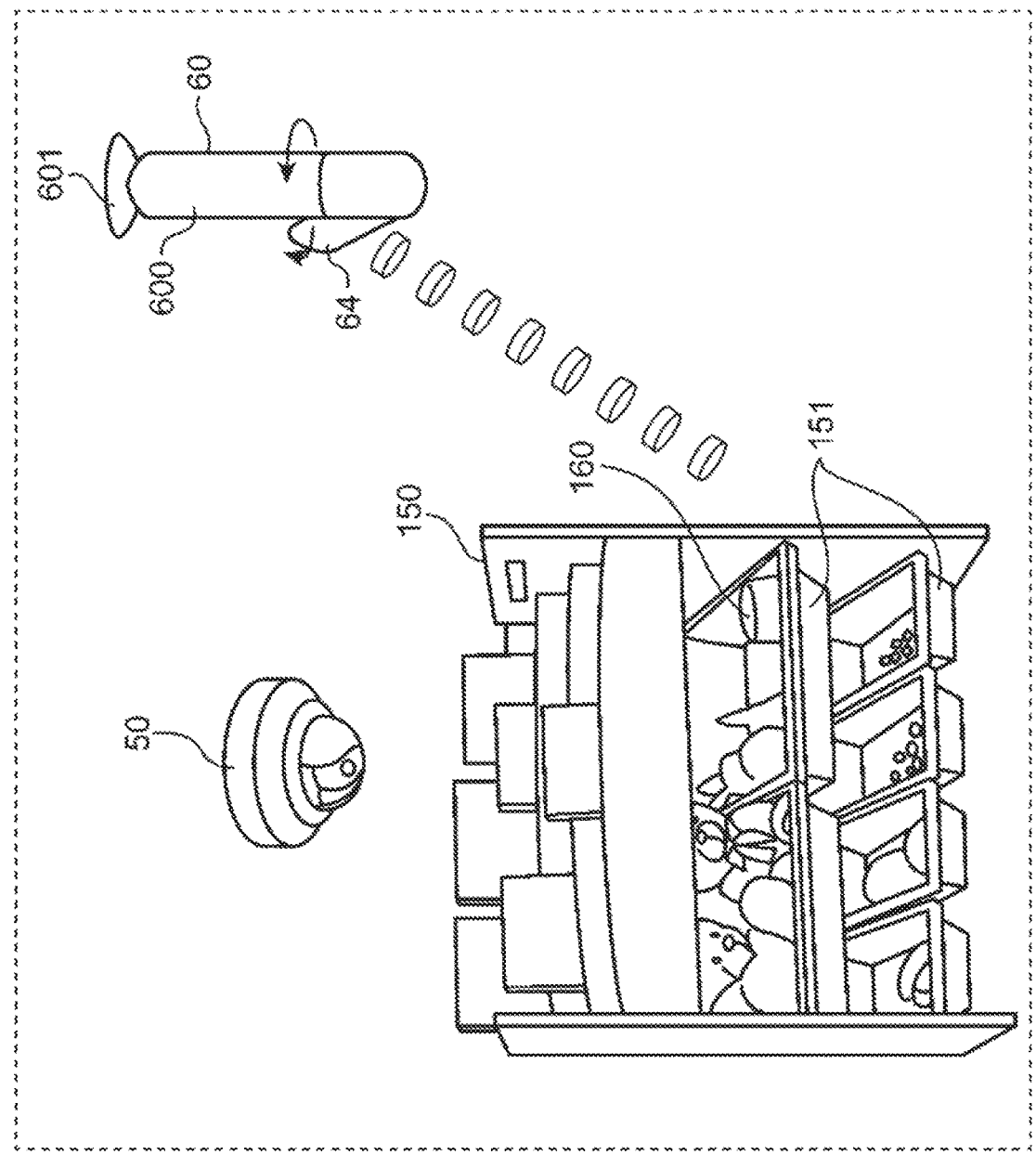
FIG. 16 is a diagram illustrating an example of the configuration of an infection risk evaluation system according to a second embodiment.

FIG. 16 is a diagram illustrating an example of the configuration of an infection risk evaluation system according to the second embodiment. The infection risk evaluation system further includes a camera 50 and a sterilization apparatus 60. The camera 50 is installed near a toy storage 150 and used to detect a toy 160 returned by the monitoring target child. The toy storage 150 is installed on a floor of a classroom of a target class and includes one or more shelves. One or more toy storage boxes 151 are provided for the shelves. The toy storage boxes 151 are boxes whose tops are open and store one or more toys 160.

The camera 50 is installed, for example, above the toy storage 150 on a ceiling of the classroom of the target class. The sterilization apparatus 60 is installed, for example, diagonally above a front side of the toy storage 150 on the ceiling of the classroom of the target class. The sterilization apparatus 60 includes a cylindrical body unit 600, a fixing unit 601 for fixing the body unit 600 on the ceiling, and a sterilization nozzle 64 that sprays a sterilization solution.

The body unit 600 is configured to be able to rotate about a longitudinal axis direction (vertical direction) relative to the fixing unit 601. The sterilization nozzle 64 is configured to be able to slide in a longitudinal axis direction relative to the body unit 600.

As a result, the sterilization apparatus 60 can adjust a direction in which the sterilization solution is sprayed to any direction relative to the front side of the toy storage 150 and spray the sterilization solution precisely onto a toy 160 to be sterilized.

Figure 17:
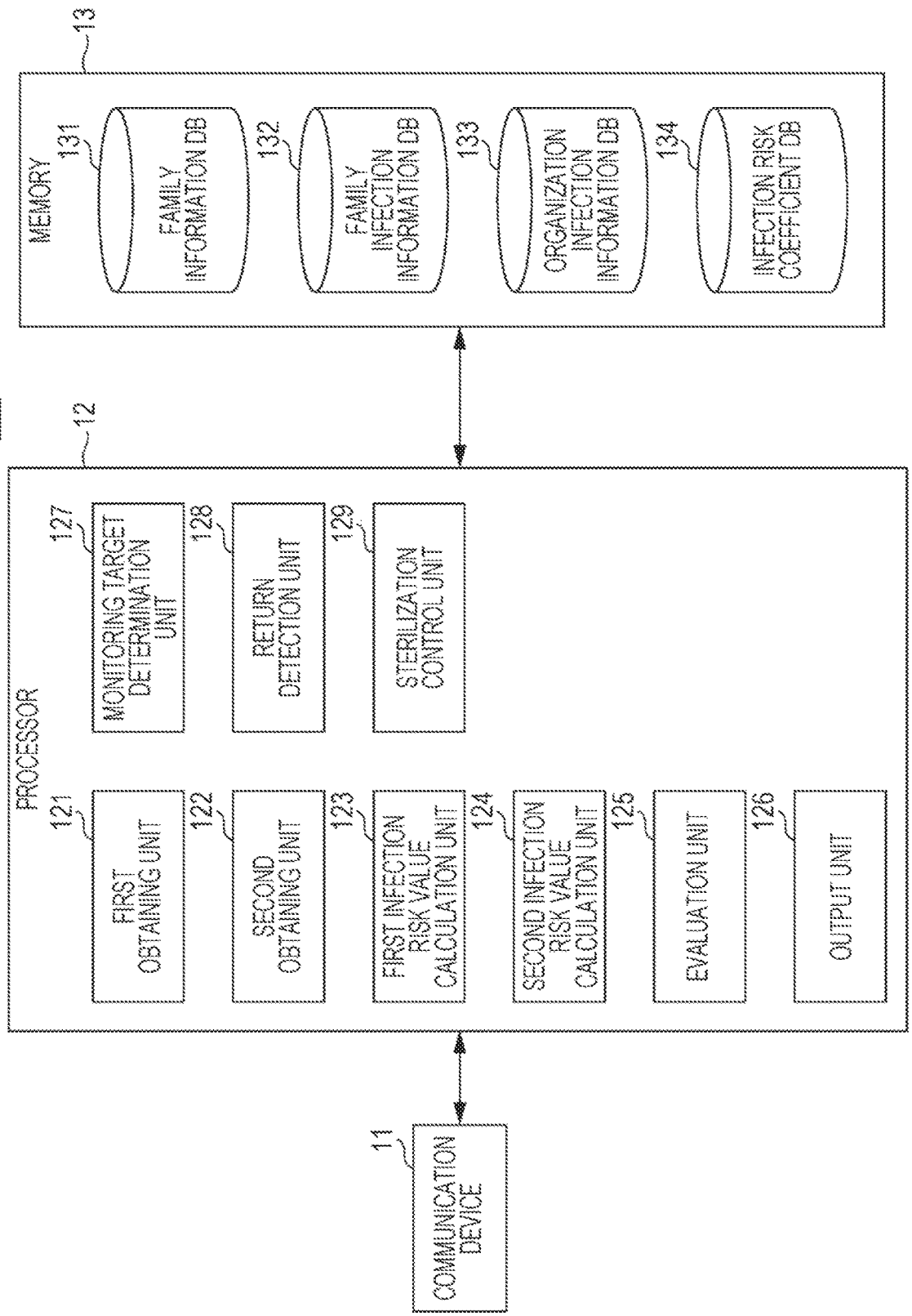
FIG. 17 is a block diagram illustrating an example of the configuration of a server according to the second embodiment of the present disclosure.

FIG. 17 is a block diagram illustrating an example of the configuration of a server 10A according to the second embodiment of the present disclosure. The server 10A includes a monitoring target determination unit 127, a return detection unit 128, and a sterilization control unit 129 in addition to the configuration according to the first embodiment.

The monitoring target determination unit 127 identifies a child whose first infection risk value is determined by the evaluation unit 125 to be larger than the first reference value as a monitoring target child. When identifying a monitoring target child, the monitoring target determination unit 127 outputs, to the camera 50 installed in a children's facility to which the monitoring target child belongs through the communication device 11, a request to transmit a surrounding image.

The communication unit 503 of the camera 50 receives the request, and the processor 501 of the camera 50 periodically transmits a surrounding image captured by the image sensor 502 at a certain frame rate to the server 10A through the communication unit 503.

After the monitoring target determination unit 127 determines a monitoring target child, the return detection unit 128 determines whether the surrounding image of the toy storage 150 transmitted from the camera 50 includes the monitoring target child. Here, the return detection unit 128 reads a face image of the monitoring target child from the family information DB 131, calculates a matching level between a feature value of a face image included in the surrounding image and a feature value of the face image of the monitoring target child, and, if the matching level is equal to or higher than a certain threshold, determines that the surrounding image includes the monitoring target child. From this time on, the return detection unit 128 detects whether the monitoring target child has returned a toy 160 to the toy storage 150 by analyzing motion of the monitoring target child in the surrounding image transmitted from the camera 50. If detecting that an object held by a hand of the monitoring target child has left the hand and moved to the toy storage boxes 151, the return detection unit 128 may determine that the toy 160 has been returned.

If the return detection unit 128 detects that the toy 160 has been returned, the sterilization control unit 129 identifies the toy 160 to be sterilized from the surrounding image captured by the camera 50 using a feature value of the returned toy 160 extracted by the return detection unit 128 from the surrounding image and identifies coordinates of the identified toy 160 on the surrounding image. The sterilization control unit 129 then determines, from the identified coordinates, a direction in which the sterilization nozzle 64 is to spray the sterilization solution, generates a sterilization command for controlling the sterilization apparatus 60 such that the sterilization solution is sprayed in the direction, and transmits the sterilization command to the sterilization apparatus 60 using the communication device 11.

Here, the sterilization control unit 129 includes a table storing, for example, coordinates on a surrounding image, rotational positions of the body unit 600 from a home position, and slide positions of the sterilization nozzle 64 from a home position while associating the coordinates, the rotational positions, and the slide positions with one another. The sterilization control unit 129 reads a rotational position and a slide position corresponding to identified coordinates from the table. The sterilization control unit 129 may then generate a sterilization command including a first control command for positioning the sterilization nozzle 64 at the read slide position and a second control command for positioning the body unit 600 at the read rotational position and transmit the sterilization command to the sterilization apparatus 60.

Figure 18:
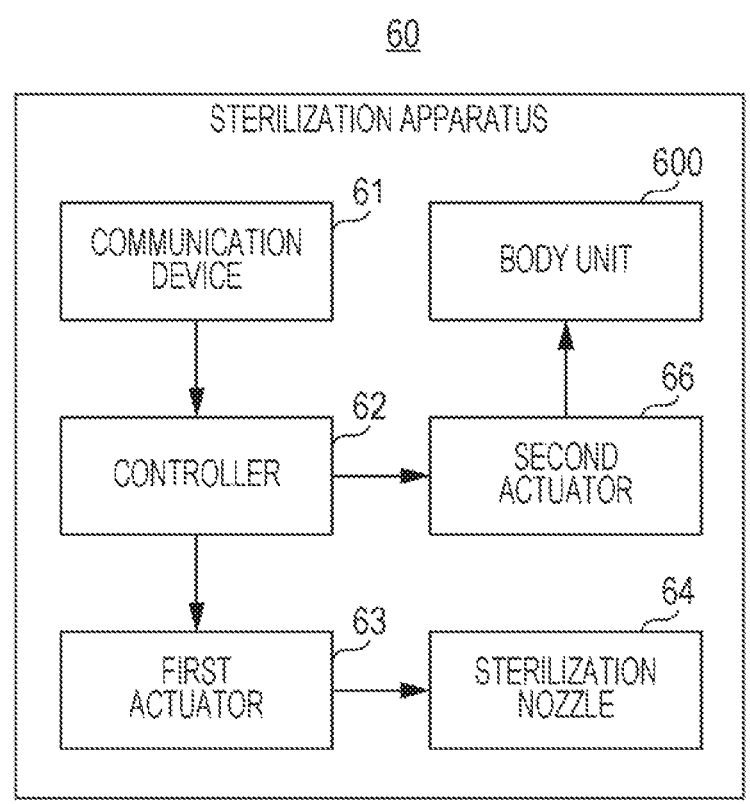
FIG. 18 is a block diagram illustrating an example of the configuration of a sterilization apparatus.

FIG. 18 is a block diagram illustrating an example of the configuration of the sterilization apparatus 60. The sterilization apparatus 60 includes a communication device 61, a controller 62, a first actuator 63, the sterilization nozzle 64, a second actuator 66, and the body unit 600. The communication device 61 is a communication device for connecting the sterilization apparatus 60 to the network NT. The controller 62 is achieved by a processor such as a CPU, for example, and controls the entirety of the sterilization apparatus 60. The first actuator 63 is achieved by a motor, for example, and slides the sterilization nozzle 64 in the longitudinal axis direction. The second actuator 66 is achieved by a motor, for example, and rotates the body unit 600 about the longitudinal axis direction.

Here, when the communication device 61 receives a sterilization command from the server 10A, the controller 62 outputs a first control command included in the sterilization command to the first actuator 63 and a second control command included in the sterilization command to the second actuator 66.

The sterilization nozzle 64 includes a fitting unit (not illustrated) slidably fitted with a groove provided in the body unit 600 and slides in the longitudinal axis direction of the body unit 600 in accordance with a first control command from the first actuator 63.

The body unit 600 rotates about the longitudinal axis direction in accordance with a second control command from the second actuator 66.

Figure 19:
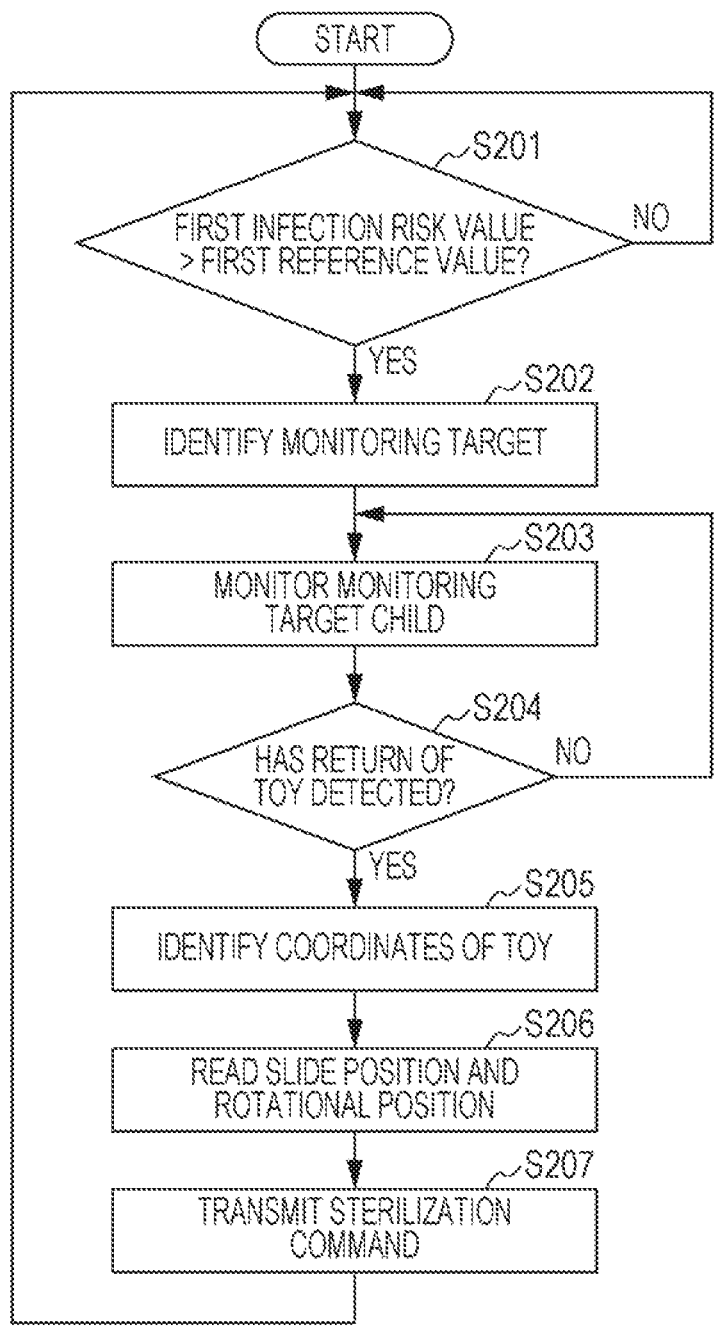
FIG. 19 is a flowchart illustrating an example of a process performed by a server according to the second embodiment.

FIG. 19 is a flowchart illustrating an example of a process performed by the server 10A according to the second embodiment. In S201, the evaluation unit 125 determines whether the first infection risk value of the target child is larger than the first reference value. If the evaluation unit 125 determines that the first infection risk value is larger than the first reference value (YES in S201), the monitoring target determination unit 127 identifies the target child as a monitoring target child (S202). If the evaluation unit 125 determines that the first infection risk value is equal to or smaller than the first reference value (NO in 3201), on the other hand, the process returns to 3201.

In S203, the return detection unit 128 monitors the monitoring target child by analyzing the surrounding image captured by the camera 50.

In S204, if detecting, as a result of the analysis of the surrounding image, that the monitoring target child has returned the toy 160 to the toy storage 150 (YES in S204), the return detection unit 128 causes the process to proceed to S205. If not detecting that the monitoring target child has returned the toy 160 (NO in S204), the return detection unit 128 causes the process to return to S203 and keeps monitoring the monitoring target child.

In S205, the sterilization control unit 129 identifies, on the surrounding image captured by the camera 50, coordinates of the returned toy 160 using a feature value of the returned toy 160.

In S206, the sterilization control unit 129 reads, from the table, a slide position and a rotational position corresponding to the coordinates of the toy 160 identified in S205.

In S207, the sterilization control unit 129 generates a sterilization command including a first control command for positioning the sterilization nozzle 64 at the read slide position and a second control command for positioning the body unit 600 at the read rotational position and transmits the sterilization command to the sterilization apparatus 60.

Upon receiving the sterilization command, the sterilization apparatus 60 outputs the first control command included in the sterilization command to the first actuator 63 and the second control command to the second actuator 66 to position the body unit 600 and the sterilization nozzle 64 at the rotational position and the slide position, respectively. The sterilization apparatus 60 then begins to spray the sterilization solution. As a result, the sterilization solution is precisely sprayed onto the returned toy 160. Here, the sterilization apparatus 60 may spray the sterilization solution for a predetermined period of time.

With the infection risk evaluation system according to the second embodiment, when a toy 160 used by a monitoring target child is returned to the toy storage 150, the toy 160 is sterilized. Contact infection, therefore, can be prevented.

Since the sterilization apparatus 60 precisely sprays the sterilization solution onto a returned toy 160, a smell of the sterilization solution does not spread over a classroom and make children uncomfortable, compared to when the sterilization solution is sprayed over the entirety of the toy storage 150 or across the classroom. In addition, consumption of the sterilization solution is minimized, and the sterilization solution is saved.

Modifications

The present disclosure may employ the following modifications.

(1) Although family infection information is input by the guardian terminal 20 in the first embodiment, the present disclosure is not limited to this. Family infection information may be input as a result of an analysis of a sound conducted by a smart speaker installed in a house, instead. In this case, if the first obtaining unit 121 detects an utterance indicating that a family member is infected with an infectious disease from the result of an analysis of a sound transmitted from the smart speaker, the first obtaining unit 121 determines that the family member is infected with the infectious disease. The first obtaining unit 121 may then input "1" to the "infection" field of the family member in the family infection information DB 132, Here, the utterance indicating that a family member is infected with an infectious disease may be, for example, "A (e.g., a younger brother) has caught the flu". In addition, because a speaker needs to be identified in order to achieve this, voiceprint data regarding family members may be registered to the family information DB 131 in advance.

(2) Although the smart speaker 30 installed in an organization to which a family member belongs obtains organization infection information in the first embodiment, the present disclosure is not limited to this. For example, a manager of the organization may input organization infection information, instead.

In this case, the manager of the organization may input information indicating whether an infectious disease is prevalent in the organization and information indicating a name of the infectious disease and transmit these pieces of information to the server 10 as organization infection information at certain time intervals (e.g., every day) using a computer (a mobile terminal or a personal computer) owned thereby. Upon receiving the organization infection information, the second obtaining unit 122 of the server 10 may update the organization infection information DB 133 with the transmitted organization infection information.

(3) Although the server 10A detects whether a monitoring target child has returned a toy 160 and transmits a sterilization command to the sterilization apparatus 60 in the second embodiment, the present disclosure is not limited to this. The sterilization apparatus 60 may perform these processes, instead.

More specifically, when the monitoring target determination unit 127 determines a monitoring target child, the sterilization apparatus 60 receives a feature value of a face of the monitoring target child from the server 10A. The controller 62 of the sterilization apparatus 60 then obtains a surrounding image from the camera 50 and monitors the monitoring target child using the feature value of the face of the monitoring target child on the obtained surrounding image. If it is detected that the monitoring target child has returned the toy 160, the controller 62 may generate the above-described first control command and second control command and transmit the first and second control commands to the first actuator 63 and the second actuator 66, respectively.

In this case, the sterilization apparatus 60 and the camera 50 may be communicably connected to each other over, for example, a local network. The controller 62 may include a table on which coordinates of returned toys 160, slide positions of the sterilization nozzle 64, and rotational positions of the body unit 600 are associated with one another.

The present disclosure also includes modes achieved by modifying the embodiments in various ways conceivable by those skilled in the art and modes achieved by combining together components and functions from different embodiments as desired without deviating from the scope of the present disclosure.

A method for evaluating an infection risk in the present disclosure also includes a following embodiment.

A method for evaluating an infection risk in an infection risk evaluation system that evaluates an infection risk by an infectious disease in a facility, a computer of the infection risk evaluation system performing a process comprising:

obtaining infection information, which is information regarding a condition of infection of each of one or more family members of a facility visitor with the infectious disease;

obtaining prevalence information, which is information regarding a condition of prevalence of the infectious disease in one or more organizations to which the one or more family members belong;

calculating a first infection risk value, which indicates a degree of an infection risk that the facility visitor is infected with the infectious disease, on a basis of the infection information, the prevalence information, and one or more first infection risk coefficients, which are obtained by expressing infection risks between the facility visitor and the one or more family members in numbers;

calculating, on a basis of the first infection risk value, a second infection risk value, which indicates a degree of the facility visitor's infection risk of being infected with the infectious disease in a group at the facility visited by the facility visitor;

performing at least either first evaluation, in which the first infection risk value is compared with a certain first reference value and the infection risk that the facility visitor is infected with the infectious disease is evaluated, and second evaluation, in which the second infection risk value is compared with a certain second reference value and the facility visitor's infection risk of being infected with the infectious disease in the group is evaluated; and outputting an evaluation result of at least either the first evaluation or the second evaluation.

Specific examples of the "facility" in the above embodiment include schools such as junior high schools and high schools, offices, and elderly care facilities. Specific examples of the "facility visitor" in the above embodiment include students when the facility is a school, commuting workers when the facility is an office, and visitors when the facility is an elderly care facility.

According to the present invention, an infection risk by an infectious disease can be accurately estimated. The present invention is therefore effective in suppressing prevalence of the infectious disease.

What is claimed is:

1. A method for evaluating an infection risk in an infection risk evaluation system that evaluates an infection risk by an infectious disease in a children's facility, the method comprising:

obtaining infection information, which is information regarding a condition of infection of each of one or more family members of a child with the infectious disease;

obtaining prevalence information, which is information regarding a condition of prevalence of the infectious disease in one or more organizations to which the one or more family members belong;

calculating a first infection risk value, which indicates a degree of an infection risk that the child is infected with the infectious disease, on a basis of the infection information, the prevalence information, and one or more first infection risk coefficients indicating one or more infection risks between the child and the one or more family members in one or more numbers;

calculating, on a basis of the first infection risk value, a second infection risk value, which indicates a degree of the child's infection risk of being infected with the infectious disease in a group at the children's facility to which the child belongs;

performing at least either first evaluation, in which the first infection risk value is compared with a certain first reference value and the infection risk that the child is infected with the infectious disease is evaluated, and second evaluation, in which the second infection risk value is compared with a certain second reference value and the child's infection risk of being infected with the infectious disease in the group is evaluated;

outputting an evaluation result of at least either the first evaluation or the second evaluation;

identifying the child whose first infection risk value is larger than the first reference value as a monitoring target child;

detecting, using a camera installed in the children's facility, whether the monitoring target child has returned a toy to a toy storage; and spraying, if it is detected that the monitoring target child has returned a toy, a sterilization solution onto the toy from a sterilization apparatus.

2. The method according to claim 1, wherein, with each of the one or more family members, a first value, which indicates that the family member is infected with the infectious disease, and a second value, which indicates that the infectious disease is prevalent in the corresponding organization, are associated in the infection information at certain time intervals, wherein the first infection risk value is calculated by adding up, at the certain time intervals, a first sum of one or more first products of the one or more first values and the one or more first infection risk coefficients corresponding to the one or more first values of all of the one or more family members and a second sum of one or more second products of the one or more second values and the one or more second infection risk coefficients corresponding to the one or more second values of all of the one or more family members, and wherein the one or more second infection risk coefficients are obtained by expressing, for the one or more family members, the infection risks in relation to the one or more organization in numbers.

3. The method according to claim 2, wherein the second infection risk value is obtained by calculating, at the certain time intervals, a sum of first infection risk values calculated for children belonging to the group or an average of the sum.

4. The method according to claim 2, wherein, in a case where the first infection risk value tends to increase, the first infection risk value is increased through correction, and in a case where the first infection risk value tends to decrease, the first infection risk value is decreased through correction.

5. The method according to claim 2, further comprising:

obtaining a result of recognition of a sound performed by a sound recognition apparatus installed in each of the one or more organizations, wherein the prevalence information includes, for each of the one or more organizations, a third value, which indicates prevalence of the infectious disease, determined at the certain time intervals using the result of the recognition of a sound, and wherein the second value is generated using the third value.

6. The method according to claim 1, wherein the evaluation result of the first evaluation is output to a manager terminal owned by a manager of the group and the evaluation result of the second evaluation is output to a guardian terminal owned by a guardian of the child.

7. The method according to claim 1, wherein the evaluation result of the first evaluation includes temporal changes in the first infection risk value, and wherein the evaluation result of the second evaluation includes temporal changes in the second infection risk value.

8. The method according to claim 2, wherein, in the infection information, the first value is obtained from a guardian terminal owned by a guardian of the child.

9. An infection risk evaluation system that evaluates an infection risk by an infectious disease in a children's facility, the infection risk evaluation system comprising:

a processor; and a non-transitory memory having stored executable instructions, which when executed cause the processor to perform:

obtaining infection information, which is information regarding a condition of infection of each of one or more family members of a child with the infectious disease;

obtaining prevalence information, which is information regarding a condition of prevalence of the infectious disease in one or more organizations to which the one or more family members belong;

calculating a first infection risk value, which indicates a degree of an infection risk that the child is infected with the infectious disease, on a basis of the infection information, the prevalence information, and one or more first infection risk coefficients indicating one or more infection risks between the child and the one or more family members in one or more numbers;

calculating, on a basis of the first infection risk value, a second infection risk value, which indicates a degree of the child's infection risk of being infected with the infectious disease in a group at the children's facility to which the child belongs;

performing at least either first evaluation, in which the first infection risk value is compared with a certain first reference value and the infection risk that the child is infected with the infectious disease is evaluated, and second evaluation, in which the second infection risk value is compared with a certain second reference value and the child's infection risk of being infected with the infectious disease in the group is evaluated; and outputting an evaluation result of at least either the first evaluation or the second evaluation;

identifying the child whose first infection risk value is larger than the first reference value as a monitoring target child;

detecting, using a camera installed in the children's facility, whether the monitoring target child has returned a toy to a toy storage; and spraying, if it is detected that the monitoring target child has returned a toy, a sterilization solution onto the toy from a sterilization apparatus.

10. A non-transitory computer-readable medium storing a program for causing a computer to perform a method, the method comprising:
- obtaining infection information, which is information regarding a condition of infection of each of one or more family members of a child with an infectious disease;
- obtaining prevalence information, which is information regarding a condition of prevalence of the infectious disease in one or more organizations to which the one or more family members belong;
- calculating a first infection risk value, which indicates a degree of an infection risk that the child is infected with the infectious disease, on a basis of the infection information, the prevalence information, and one or more first infection risk coefficients, which are obtained by expressing infection risks between the child and the one or more family members in numbers;
- calculating, on a basis of the first infection risk value, a second infection risk value, which indicates a degree of the child's infection risk of being infected with the infectious disease in a group at the children's facility to which the child belongs;
- performing at least either first evaluation, in which the first infection risk value is compared with a certain first reference value and the infection risk that the child is infected with the infectious disease is evaluated, and second evaluation, in which the second infection risk value is compared with a certain second reference value and the child's infection risk of being infected with the infectious disease in the group is evaluated;
- outputting an evaluation result of at least either the first evaluation or the second evaluation;
- identifying the child whose first infection risk value is larger than the first reference value as a monitoring target child;
- detecting, using a camera installed in the children's facility, whether the monitoring target child has returned a toy to a toy storage; and
- spraying, if it is detected that the monitoring target child has returned a toy, a sterilization solution onto the toy from a sterilization apparatus.

11. A method for evaluating an infection risk in an infection risk evaluation system that evaluates an infection risk by an infectious disease in a facility, the method comprising:
- obtaining infection information, which is information regarding a condition of infection of each of one or more family members of a facility visitor with the infectious disease;
- obtaining prevalence information, which is information regarding a condition of prevalence of the infectious disease in one or more organizations to which the one or more family members belong;
- calculating a first infection risk value, which indicates a degree of an infection risk that the facility visitor is infected with the infectious disease, on a basis of the infection information, the prevalence information, and one or more first infection risk coefficients indicating one or more infection risks between the facility visitor and the one or more family members in one or more numbers;
- calculating, on a basis of the first infection risk value, a second infection risk value, which indicates a degree of the facility visitor's infection risk of being infected with the infectious disease in a group at the facility visited by the facility visitor;
- performing at least either first evaluation, in which the first infection risk value is compared with a certain first reference value and the infection risk that the facility visitor is infected with the infectious disease is evaluated, and second evaluation, in which the second infection risk value is compared with a certain second reference value and the facility visitor's infection risk of being infected with the infectious disease in the group is evaluated;
- outputting an evaluation result of at least either the first evaluation or the second evaluation;
- identifying the facility visitor whose first infection risk value is larger than the first reference value as a monitoring target facility visitor;
- detecting, using a camera installed in the children's facility, whether the monitoring target facility visitor has returned an object to a storage; and
- spraying, if it is detected that the monitoring target facility visitor has returned the object, a sterilization solution onto the object from a sterilization apparatus.

12. A method for evaluating an infection risk, the method comprising:
- processes repeated by a computer n times while changing k from 1 to n, k and n being natural numbers, n being two or more,
- wherein the processes include first to sixth processes,
- wherein, in the first process, k-th infection information is obtained,
- wherein, in the second process, k-th prevalence information is obtained,
- wherein, in the third process, Ro(k) indicating a degree of probability that a k-th child is currently infected is calculated, on a basis of the k-th infection information, the k-th prevalence information, and k-th infection risk coefficients,
- wherein, in the fourth process, k-th information based on a comparison between the Ro(k) and a first predetermined value is transmitted to a terminal owned by a person in charge of a class to which children including the k-th child belong, the children being first to n-th children,
- wherein, in the fifth process, $(Ro(1) \ldots +Ro(k-1)+Ro(k+1) \ldots +Ro(n))/(n-1)$ being an infection risk value indicating a degree of probability that the k-th child is infected with the k-th child attending the class, is calculated,
- wherein, in the sixth process, (n+k)th information based on a comparison between the infection risk value and a second predetermined value is transmitted to a terminal of a k-th person,
- wherein the k-th infection information indicates infectious disease infection conditions of k-th persons living with the k-th child,
- wherein the k-th persons living with the k-th child include the k-th person,
- wherein the k-th prevalence information indicates k-th infectious disease prevalence conditions in k-th buildings regularly visited by the k-th persons living with the k-th child,
- wherein the k-th persons living with the k-th child and the k-th infectious disease prevalence conditions in the k-th buildings are in one-to-one correspondence,
- wherein the k-th infection risk coefficients indicate intimacy levels between the k-th child and the k-th persons living with the k-th child, wherein the k-th persons living with the k-th child and the k-th infection risk coefficients are in one-to-one correspondence, wherein a day nursery, a kindergarten, or an elementary school includes the class, and wherein the method further comprises:
- identifying a child whose infection risk value is larger than a reference value as a monitoring target child;
- detecting, using a camera installed in the class, whether the monitoring target child has returned a toy to a toy storage; and
- spraying, if it is detected that the monitoring target child has returned a toy, a sterilization solution onto the toy from a sterilization apparatus.

* * * * *